United States Patent
Deak et al.

(10) Patent No.: US 9,126,935 B2
(45) Date of Patent: Sep. 8, 2015

(54) AURORA KINASE MODULATORS AND METHODS OF USE

(75) Inventors: Holly L. Deak, Brookline, MA (US); Brian L. Hodous, Cambridge, MA (US); Jason B. Human, Boston, MA (US); Hanh Nho Nguyen, Arlington, MA (US); Karina Romero, Arlington, MA (US)

(73) Assignee: Amgen Inc., Thousand Oaks, CA (US)

( * ) Notice: Subject to any disclaimer, the term of this patent is extended or adjusted under 35 U.S.C. 154(b) by 631 days.

(21) Appl. No.: 13/058,616

(22) PCT Filed: Aug. 7, 2009

(86) PCT No.: PCT/US2009/053160
§ 371 (c)(1),
(2), (4) Date: Aug. 23, 2011

(87) PCT Pub. No.: WO2010/019473
PCT Pub. Date: Feb. 18, 2010

(65) Prior Publication Data
US 2011/0294837 A1  Dec. 1, 2011

Related U.S. Application Data

(60) Provisional application No. 61/088,968, filed on Aug. 14, 2008.

(51) Int. Cl.

| | | |
|---|---|---|
| A61K 31/505 | (2006.01) |
| A61K 31/44 | (2006.01) |
| A61K 31/47 | (2006.01) |
| C07D 239/02 | (2006.01) |
| C07D 215/04 | (2006.01) |
| C07D 213/78 | (2006.01) |
| C07D 471/02 | (2006.01) |
| C07D 215/22 | (2006.01) |
| C07D 239/34 | (2006.01) |

(52) U.S. Cl.
CPC ............ *C07D 215/22* (2013.01); *C07D 239/34* (2013.01)

(58) Field of Classification Search
CPC ..... A61K 31/44; A61K 31/47; A61K 31/505; C07D 239/02; C07D 471/02; C07D 215/04; C07D 213/78
USPC ........... 514/272, 300, 312; 544/321; 546/153, 546/298, 122
See application file for complete search history.

(56) References Cited

U.S. PATENT DOCUMENTS

| 6,143,764 A | 11/2000 | Kubo et al. |
| 6,903,101 B1 | 6/2005 | Dumas |
| 6,919,338 B2 | 7/2005 | Mortlock et al. |
| 7,307,088 B2 | 12/2007 | Hung et al. |
| 2009/0285772 A1 * | 11/2009 | Phiasivongsa et al. ...... 424/85.2 |

FOREIGN PATENT DOCUMENTS

| EP | 1752457 A1 | 2/2007 |
| WO | 9713771 A1 | 4/1997 |
| WO | 9802434 A1 | 1/1998 |
| WO | 9802437 A1 | 1/1998 |
| WO | 0050405 A1 | 8/2000 |
| WO | 0071129 A1 | 11/2000 |
| WO | 0110859 A1 | 2/2001 |
| WO | 0121597 A1 | 3/2001 |
| WO | 0194353 A1 | 12/2001 |
| WO | 0200649 A1 | 1/2002 |
| WO | 02092087 A1 | 11/2002 |
| WO | 03055491 A1 | 7/2003 |

(Continued)

OTHER PUBLICATIONS

R. Giet and C. Prigent, J. Cell. Sci., 112:3591-3601 (1999).

(Continued)

*Primary Examiner* — James O. Wilson
*Assistant Examiner* — Ebenezer O Sackey
(74) *Attorney, Agent, or Firm* — G. Prabhakar Reddy

(57) ABSTRACT

The present invention relates to chemical compounds having a general formula I

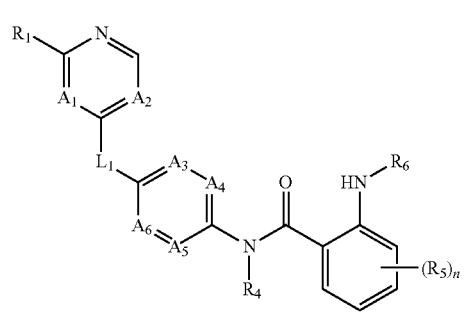

wherein $A^{1-6}$, $L^1$, $R^1$, $R^{4-6}$ and n are defined herein, and synthetic intermediates, which are capable of modulating various protein kinase receptor enzymes and, thereby, influencing various disease states and conditions related to the activities of such kinases. For example, the compounds are capable of modulating Aurora kinase thereby influencing the process of cell cycle and cell proliferation to treat cancer and cancer-related diseases. The invention also includes pharmaceutical compositions, including the compounds and methods of treating disease states related to the activity of Aurora kinase.

13 Claims, No Drawings

(56) References Cited

FOREIGN PATENT DOCUMENTS

| WO | 03082208 A2 | 10/2003 |
| WO | 03082289 A1 | 10/2003 |
| WO | 2004000833 A1 | 12/2003 |
| WO | 2004016612 A1 | 2/2004 |
| WO | 2004037814 A1 | 5/2004 |
| WO | 2004039774 A1 | 5/2004 |
| WO | 2005030144 A2 | 4/2005 |
| WO | 2005047279 A1 | 5/2005 |
| WO | 2005118572 A1 | 12/2005 |
| WO | 2005121125 A1 | 12/2005 |
| WO | 2006085330 A1 | 8/2006 |
| WO | 2007084815 A1 | 7/2007 |
| WO | 2007087276 A1 | 8/2007 |
| WO | 2008124083 A1 | 10/2008 |

OTHER PUBLICATIONS

Y. Miyoshi et al., Int. J. Cancer, 92:370-373 (2001).
Angew. Chem. Int. Ed. 2003, 42, 5993-5996.
Garnier, E.; Andoux, J.; Pasquinet, E.; Suzenet, F.; Poullain, D.; Lebret, B.; Guillaumet, G. J. Org. Chem. 2004, 69, 7809.

* cited by examiner

AURORA KINASE MODULATORS AND METHODS OF USE

RELATED APPLICATIONS

This application is a US national application entry via 35 USC §371(c) of PCT/US2009/053160, filed on Aug. 7, 2009, which PCT application claims the benefit of U.S. Provisional Patent Application No. 61/088,968, filed Aug. 14, 2008, both specifications of which are hereby incorporated herein by reference in their entireties.

FIELD OF THE INVENTION

The invention relates to the field of pharmaceutical agents and, more specifically, is directed to compounds and compositions useful for modulating Aurora kinase, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different cancers, numerous groups, over the last couple of decades, have invested a tremendous amount of time, effort and financial resources. However, to date, only a few of the available cancer treatments and therapies offer any considerable degree of success.

Cancer is often characterized by unregulated cell proliferation. Damage to one or more genes, responsible for the cellular pathways, which control progress of proliferation through the cell cycle, typically causes the loss of normal regulation of cell proliferation. These genes code for various proteins, which participate in a cascade of events, including protein phosphorylation, leading to cell-cycling progression and cell proliferation. Various kinase proteins have been identified, which play roles in the cell cycling cascade and in protein phosphorylation in particular.

One class of proteins found to play a part in cell cycling and, therefore, cell proliferation is the Aurora kinase family of proteins. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also commonly referred to as Aurora 2, Aurora 1, and Aurora 3, respectively.

The specific function of each Aurora kinase member in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases appear to be viable targets for the treatment of cancer. Aurora kinases are overexpressed in various types of cancers, including colon, breast, lung, pancrease, prostate, bladder, head, neck, cervix, and ovarion cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

Further, inhibition of one or more of the Aurora kinases by several parties has been shown to inhibit cell proliferation and trigger apoptosis in several tumor cell lines. Particularly, inhibition of Aurora has been found to arrest cell cycling and promote programmed cell death via apoptosis. Accordingly, there has been a strong interest in finding inhibitors of Aurora kinase proteins.

Thus, the inhibition of Aurora kinases has been regarded as a promising approach for the development of novel anti-cancer agents. For example, WO 04/039774 describes aza-quinazolinones for treating cancer via inhibiton of Aurora kinase, WO 04/037814 describes indazolinones for treating cancer via inhibiton of Aurora kinase, WO 04/016612 describes 2,6,9-substituted purine derivatives for treating cancer via inhibiton of Aurora kinase, WO 04/000833 describes tri- and tetra-substituted pyrimidine compounds useful for treating Aurora-mediated diseases, WO 04/092607 describes crystals useful for screening, designing and evaluating compounds as agonists or antagonists of Aurora kinase and U.S. Pat. No. 6,919,338 and WO 03/055491 each describe substituted quinazoline derivatives as inhibitors of Aurora kinase.

BRIEF DESCRIPTION OF THE INVENTION

The present invention provides a new class of compounds useful for modulating one or more of the Aurora kinase enzymes and for treating Aurora kinase-mediated conditions and/or diseases, including cancer. In one embodiment of the invention, the compounds, including pharmaceutically acceptable salts thereof, are generally defined by Formula I

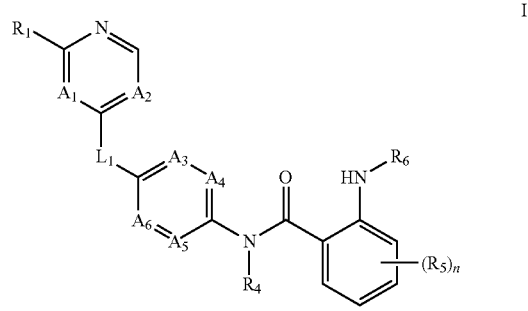

wherein $A^{1-6}$, $L^1$, $R^1$, $R^{4-6}$ and n are defined herein.

In another embodiment, the invention provides compounds of Formula II, which are similar in structure to Formula I above.

The invention also provides processes for making compounds of Formulas I-II, as well as intermediates useful in such processes.

The compounds provided by the invention have Aurora kinase modulatory activity and, in particular, Aurora kinase inhibitory activity. To this end, the invention also provides the use of these compounds, as well as pharmaceutically acceptable salts thereof, in the preparation and manufacture of a pharmaceutical composition or medicament for therapeutic, prophylactic, acute or chronic treatment of Aurora kinase mediated diseases and disorders, including without limitation, cancer. Thus, the compounds of the invention are useful in the manufacture of anti-cancer medicaments. For example, in one embodiment, the invention provides a pharmaceutical composition (also referred to herein as a medicament) comprising a therapeutically-effective amount of a compound of Formula I or II in association with at least one pharmaceutically-acceptable carrier, adjuvant or diluent.

DETAILED DESCRIPTION OF THE INVENTION

In one embodiment of the invention, compounds useful for treating Aurora kinase and related disorders, including cancer and inflammation, are defined by Formula I:

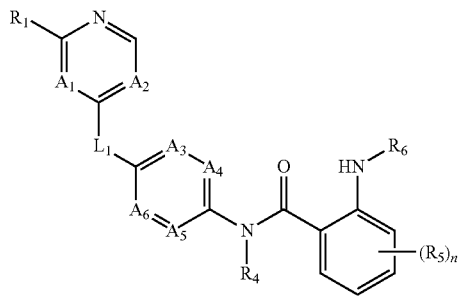

I or a stereoisomer, a tautomer, a solvate, a pharmaceutically acceptable salt or prodrug thereof, wherein each of $A^1$ and $A^2$, independently, is N or $CR^2$, provided no more than one of $A^1$ and $A^2$ is N;

each of $A^3$, $A^4$, $A^5$ and $A^6$, independently, is N or $CR^3$, provided that no more than two of $A^3$, $A^4$, $A^5$ and $A^6$ is N;

$L^1$ is —O— or —S—;

$R^1$ is acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)_2R^7$, —$S(O)_2R^7$, —$S(O)_2NR^7R^7$, —$NR^7S(O)_2NR^7R^7$, —$NR^7S(O)_2R^7$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl and ring of said ring system is optionally substituted independently with 1-5 substituents of $R^7$;

each $R^2$, independently, is H, halo, haloalkyl, haloalkoxyl, CN, OH, SH, $NO_2$, $NH_2$, methyl, ethyl, propyl, isopropyl, $C_{1-4}$-alkylamino-, $C_{1-4}$-dialkylamino-, $C_{1-4}$-alkoxyl, $C_{1-4}$-thioalkoxyl or acetyl;

alternatively, when $A^1$ is $CR^2$, then $R^2$ and $R^1$ taken together with the carbon atoms to which they are attached form a 6-membered ring of carbon atoms optionally including one or two nitrogen atoms, and optionally substituted with 1-3 substituents of $R^{1a}$, wherein each $R^{1a}$ is halo, haloalkyl, acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$COOR^7$, —$OC(O)R^7$, —$C(O)C(O)R^7$, —$C(O)NR^7R^7$, —$NR^7C(O)$ $R^7$, —$NR^7C(O)NR^7R^7$, —$NR^7(COOR^7)$, —$OC(O)NR^7R^7$, —$S(O)_2R^7$, —$S(O)_2R^7$, —$S(O)_2NR^7R^7$, —$NR^7S(O)_2NR^7R^7$, —$NR^7S(O)_2R^7$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl and ring of said ring system is optionally substituted independently with 1-5 substituents of $R^7$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^7$;

$R^4$ is H or methyl;

each $R^5$, independently, is halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^7$;

$R^6$ is acetyl, $C_{1-10}$-alkyl, $C_{2-10}$-alkenyl, $C_{2-10}$-alkynyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl and ring of said ring system is optionally substituted independently with 1-5 substituents of $R^7$;

each $R^7$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —$C(O)NHC_{1-6}$-alkyl, —$NHC(O)C_{1-6}$-alkyl, —$S(O)C_{1-6}$-alkyl, —$S(O)_2NHC_{1-6}$-alkyl, —$NHS(O)_2C_{1-10}$-alkyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

In another embodiment, Formula I includes compounds wherein $A^1$ is N and $A^2$ is $CR^2$, in conjunction with any of the above or below embodiments.

In another embodiment, Formula I includes compounds wherein $A^1$ is $CR^2$ and $A^2$ is N, in conjunction with any of the above or below embodiments.

In another embodiment, Formula I includes compounds wherein each of $A^1$ and $A^2$ independently, is $CR^2$, in conjunction with any of the above or below embodiments.

In another embodiment, Formula I includes compounds wherein each of $A^1$ and $A^2$ independently, is $CR^2$ wherein $R^2$ is either H or a halogen, in conjunction with any of the above or below embodiments.

In another embodiment, Formula I includes compounds wherein each of $A^3$, $A^4$, $A^5$ and $A^6$ is $CR^3$, in conjunction with any of the above or below embodiments.

In another embodiment, Formula I includes compounds wherein each of $A^3$, $A^4$, $A^5$ and $A^6$, independently, is $CR^3$ and each $R^3$, independently, is H, F, Cl, Br, $CF_3$, $C_2F_5$, CN, OH, SH, NO₂, NH₂, methyl, ethyl, propyl, cyclopropyl, CH₃NH—, CH₃O—, CH₃S— or —C(O)CH₃, in conjunction with any of the above or below embodiments.

In another embodiment, Formula I includes compounds wherein three of $A^3$, $A^4$, $A^5$ and $A^6$ is CH, and one of $A^3$, $A^4$, $A^5$ and $A^6$ is $CR^3$, in conjunction with any of the above or below embodiments.

In another embodiment, Formula I includes compounds wherein each of $A^3$, $A^4$, $A^5$ and $A^6$ is CH, in conjunction with any of the above or below embodiments.

In another embodiment, Formula I includes compounds wherein at least one of $A^3$, $A^4$, $A^5$ and $A^6$, independently, is N, in conjunction with any of the above or below embodiments.

In another embodiment, Formula I includes compounds wherein $A^3$ is N and each of $A^4$, $A^5$ and $A^6$ is $CR^3$, in conjunction with any of the above or below embodiments.

In another embodiment, Formula I includes compounds wherein $A^4$ is N and each of $A^3$, $A^5$ and $A^6$ is $CR^3$, in conjunction with any of the above or below embodiments.

In another embodiment, Formula I includes compounds wherein $A^5$ is N and each of $A^3$, $A^4$ and $A^6$ is $CR^3$, in conjunction with any of the above or below embodiments.

In another embodiment, Formula I includes compounds wherein $A^6$ is N and each of $A^3$, $A^4$ and $A^4$ is $CR^3$, in conjunction with any of the above or below embodiments.

In another embodiment, Formula I includes compounds wherein each of $A^3$ and $A^6$ is N and each of $A^4$ and $A^5$ is $CR^3$, in conjunction with any of the above or below embodiments.

In another embodiment, Formula I includes compounds wherein each of $A^4$ and $A^5$ is N and each of $A^3$ and $A^6$ is $CR^3$, in conjunction with any of the above or below embodiments.

In another embodiment, Formula I includes compounds wherein each of $A^3$ and $A^4$ is N and each of $A^5$ and $A^6$ is $CR^3$, in conjunction with any of the above or below embodiments.

In another embodiment, Formula I includes compounds wherein $L^1$ is —O—, in conjunction with any of the above or below embodiments.

In another embodiment, Formula I includes compounds wherein $L^1$ is —S—, in conjunction with any of the above or below embodiments.

In another embodiment, Formula I includes compounds wherein $L^1$ is —O— or —S—, in conjunction with any of the above or below embodiments.

In another embodiment, Formula I includes compounds wherein $R^1$ is acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)R^7$, —$S(O)_2R^7$, —$S(O)_2NR^7R^7$, —$NR^7S(O)_2NR^7R^7$, —$NR^7S(O)_2R^7$, in conjunction with any of the above or below embodiments.

In another embodiment, Formula I includes compounds wherein $R^1$ is halo, haloalkyl, haloalkoxyl, CN, OH, SH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^7$, —$NR^7R^7$ or —$C(O)R^7$, in conjunction with any of the above or below embodiments.

In another embodiment, Formula I includes compounds wherein $R^1$ is —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)_2R^7$, —$S(O)_2R^7$, —$S(O)_2NR^7R^7$, —$NR^7S(O)_2NR^7R^7$, —$NR^7S(O)_2R^7$, in conjunction with any of the above or below embodiments.

In another embodiment, Formula I includes compounds wherein $R^1$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl ring of said ring system is optionally substituted independently with 1-5 substituents of $R^7$, in conjunction with any of the above or below embodiments.

In another embodiment, Formula I includes compounds wherein each $R^2$, independently, is H, halo, haloalkyl, haloalkoxyl, CN, OH, SH, NO₂, NH₂, methyl, ethyl, propyl, isopropyl, $C_{1-4}$-alkylamino-, $C_{1-4}$-dialkylamino-, $C_{1-4}$-alkoxyl, $C_{1-4}$-thioalkoxyl or acetyl, in conjunction with any of the above or below embodiments.

In another embodiment, Formula I includes compounds wherein each $R^2$, independently, is H, halo, $CF_3$, CN, NO₂, NH₂, OH, methyl, methoxyl, ethyl, ethoxyl, propyl, propoxyl, isopropyl, methylamine, dimethylamine, ethylamine, diethylamine, propylamine or isopropylamine, in conjunction with any of the above or below embodiments.

In another embodiment, Formula I includes compounds wherein each $R^2$, independently, is H, halo, haloalkyl, haloalkoxyl, OH, SH, NO₂, NH₂, $C_{1-6}$-alkyl, $C_{2-6}$-alkenyl, $C_{2-6}$-alkynyl, $C_{1-6}$-alkylamino-, $C_{1-6}$-alkoxyl, $C_{1-6}$-thioalkoxyl or —$C(O)R^7$, in conjunction with any of the above or below embodiments.

In another embodiment, Formula I includes compounds wherein
$A^1$ is $CR^2$, wherein $R^2$ and $R^1$ taken together with the carbon atoms to which they are attached form a ring of

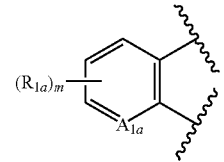

wherein $A^{1a}$ is N or CH;
$R^{1a}$ is halo, haloalkyl, acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)R^7$, —$S(O)_2R^7$, —$S(O)_2NR^7R^7$, —$NR^7S(O)_2NR^7R^7$, —$NR^7S(O)_2R^7$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^7$; and
m is 0, 1 or 2, in conjunction with any of the above or below embodiments.

In another embodiment, Formula I includes compounds wherein each of $R^1$ or $R^{1a}$, independently, is F, Cl, Br, I, $CF_3$, acetyl, methyl, ethyl, propyl, isopropyl, butyl, isobutyl, pentyl, neopentyl, —$SR^7$, methoxyl, ethoxyl, propoxyl, isopropoxyl, butoxyl, isobutoxyl, pentoxyl, —$NR^7R^7$, —$C(O)R^7$, —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)_2R^7$, —$S(O)_2R^7$, —$S(O)_2NR^7R^7$, —NR$^7$S(O)$_2$NR$^7$R$^7$, —NR$^7$S(O)$_2$R$^7$ or a ring selected from phenyl, naphthyl, pyridyl, pyrimidyl, triazinyl, pyridazinyl, pyrazinyl, furyl, thienyl, pyrrolyl, imidazolyl, triazolyl, pyrazolyl, oxazolyl, thiazolyl, isoxazolyl, isothiazolyl, morpholinyl, piperidinyl, piperazinyl, pyranyl, tetrahydrofuranyl, tetrahydropyrrolyl, cyclopropyl, cyclobutyl, cyclopentyl and cyclohexyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-5 substituents of R$^7$, in conjunction with any of the above or below embodiments.

In another embodiment, Formula I includes compounds wherein each R$^3$, independently, is H, halo, haloalkyl, haloalkoxyl, CN, OH, SH, NO$_2$, NH$_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)R$^7$, in conjunction with any of the above or below embodiments.

In another embodiment, Formula I includes compounds wherein each R$^3$, independently, is H, halo, haloalkyl, haloalkoxyl, OH, SH, NO$_2$, NH$_2$, $C_{1-6}$-alkyl, $C_{2-6}$-alkenyl, $C_{2-6}$-alkynyl, $C_{1-6}$-alkylamino-, $C_{1-6}$-alkoxyl, $C_{1-6}$-thioalkoxyl or —C(O)R$^7$, in conjunction with any of the above or below embodiments.

In another embodiment, Formula I includes compounds wherein each R$^3$, independently, is H, halo, CF$_3$, CN, NO$_2$, NH$_2$, OH, methyl, methoxyl, ethyl, ethoxyl, propyl, propoxyl, isopropyl, methylamine, dimethylamine, ethylamine, diethylamine, propylamine or isopropylamine, in conjunction with any of the above or below embodiments.

In another embodiment, Formula I includes compounds wherein R$^4$ is H or methyl, in conjunction with any of the above or below embodiments.

In another embodiment, Formula I includes compounds wherein R$^4$ is H or $C_{1-4}$alkyl, in conjunction with any of the above or below embodiments.

In another embodiment, Formula I includes compounds wherein each R$^5$, independently, is halo, haloalkyl, haloalkoxyl, CN, OH, SH, NO$_2$, NH$_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-alkoxyl, $C_{1-10}$-thioalkoxyl or —C(O)R$^7$, in conjunction with any of the above or below embodiments.

In another embodiment, Formula I includes compounds wherein each R$^5$, independently, is H, halo, CF$_3$, CN, NO$_2$, NH$_2$, OH, methyl, methoxyl, ethyl, ethoxyl, propyl, propoxyl, isopropyl, methylamine, dimethylamine, ethylamine, diethylamine, propylamine or isopropylamine, in conjunction with any of the above or below embodiments.

In another embodiment, Formula I includes compounds wherein R$^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of R$^7$, halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula I includes compounds wherein R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, benzodioxolyl, hexahydropyrrolo[1,2-a]pyrazinyl, tetrahydropyrrolyl, pyrrolidinyl, piperidinyl, morpholinyl, piperazinyl, tetrahydrofuranyl, cyclopropyl, cyclobutyl, azetidinyl, cyclopentyl, cyclohexyl, cycloheptyl or pyranyl, each of which is optionally substituted independently with 1-5 substituents of R$^7$, halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-dialkylamino-, benzyl or phenyl, in conjunction with any of the above or below embodiments.

In another embodiment, Formula I includes compounds wherein R$^6$ is halo, haloalkyl, haloalkoxyl, CN, OH, SH, NO$_2$, NH$_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, SR$^8$, OR$^8$, NR$^8$R$^8$, C(O)R$^8$, COOR$^8$, C(O)NR$^8$R$^8$, NR$^8$C(O)R$^8$, NR$^8$C(O)NR$^8$R$^8$, NR$^8$ (COOR$^8$), S(O)$_2$R$^8$, S(O)$_2$NR$^8$R$^8$, NR$^8$S(O)$_2$R$^8$, NR$^8$S(O)$_2$NR$^8$R$^8$, in conjunction with any of the above or below embodiments.

In another embodiment, Formula I includes compounds wherein each of A$^1$ and A$^2$, independently, is CR$^2$, and each R$^2$, independently, is H, F, Cl, Br, CF$_3$, CN, OH, SH, NO$_2$, NH$_2$, methyl, ethyl, CH$_3$NH—, CH$_3$O—, CH$_3$S— or —C(O)CH$_3$; and R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, tetrahydropyrrolyl, pyrrolidinyl, piperidinyl, morpholinyl, piperazinyl, tetrahydrofuranyl, cyclopropyl, cyclobutyl, azetidinyl, cyclopentyl, cyclohexyl, cycloheptyl or pyranyl, each of which is optionally substituted independently with 1-5 substituents of halo, haloalkyl, haloalkoxyl, CN, NO$_2$, NH$_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, the compounds of the present invention include compounds of Formula II:

II

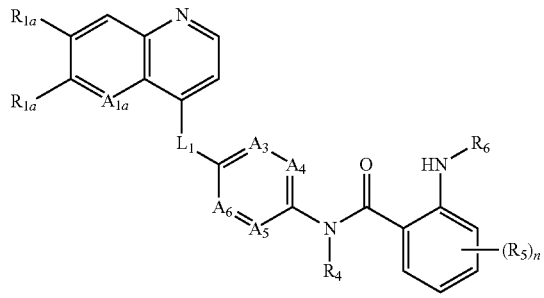

or a pharmaceutically acceptable salt thereof, wherein $A^{1a}$ is N or $CR^2$, wherein $R^2$ is H, F, Cl, Br, $CF_3$, CN, OH, SH, $NO_2$, $NH_2$, methyl, ethyl, $CH_3NH$—, $CH_3O$—, $CH_3S$— or —$C(O)CH_3$;

each of $A^3$, $A^4$, $A^5$ and $A^6$, independently, is N or $CR^3$, provided that no more than two of $A^3$, $A^4$, $A^5$ and $A^6$ is N;

$L^1$ is —O— or —S—;

each $R^{1a}$, independently, is H, acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$C(O)NR^7R^7$, —$NR^7C(O)R^7$, —$NR^7C(O)NR^7R^7$, —$NR^7(COOR^7)$, —$S(O)_2R^7$, —$S(O)_2R^7$, —$S(O)_2NR^7R^7$, —$NR^7S(O)_2NR^7R^7$, —$NR^7S(O)_2R^7$ or a fully saturated or partially or fully unsaturated 3-8 membered monocyclic or a 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl and ring of said ring system is optionally substituted independently with 1-5 substituents of $R^7$;

each $R^3$, independently, is H, F, Cl, Br, $CF_3$, $C_2F_5$, CN, OH, SH, $NO_2$, $NH_2$, methyl, ethyl, propyl, cyclopropyl, $CH_3NH$—, $CH_3O$—, $CH_3S$— or —$C(O)CH_3$;

$R^4$ is H or methyl;

each $R^5$, independently, is halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^7$;

$R^6$ is acetyl, $C_{1-10}$-alkyl, $C_{2-10}$-alkenyl, $C_{2-10}$-alkynyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl and ring of said ring system is optionally substituted independently with 1-5 substituents of $R^7$;

each $R^7$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —$C(O)NHC_{1-6}$-alkyl, —$NHC(O)C_{1-6}$-alkyl, $S(O)C_{1-6}$-alkyl, $S(O)_2NHC_{1-6}$-alkyl, $NHS(O)_2C_{1-10}$-alkyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

In another embodiment, Formula II includes compounds wherein each $R^{1a}$, independently, is H, halo, $CF_3$, $C_2F_5$, haloalkoxyl, CN, OH, SH, $NO_2$, $NH_2$, acetyl, methyl, methoxyl, ethyl, ethoxyl, propyl, propoxyl, isopropyl, cyclopropyl, butyl, isobutyl, tert-butyl, cyclobutyl, pentyl, cyclopentyl, hexyl, cyclohexyl, methylamine, dimethylamine, ethylamine, diethylamine, propylamine, isopropylamine, dipropylamine, diisopropylamine, —$C(O)R^7$, —$COOR^7$, —$C(O)NHR^7$, —$NHC(O)R^7$, —$NHC(O)NHR^7$, —$NH(COOR^7)$, —$S(O)_2R^7$, —$S(O)_2R^7$, —$S(O)_2NHR^7$, —$NHS(O)_2NHR^7$, —$NHS(O)_2R^7$ or a ring selected from phenyl, pyridyl, pyrimidinyl, pyridazinyl, pyazinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl, cycloheptyl or pyranyl, said ring optionally substituted independently with 1-5 substituents of $R^7$, in conjunction with any of the above or below embodiments.

In another embodiment, Formula II includes compounds wherein $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^7$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula II includes compounds wherein $L^1$ is —O— or —S—;

each $R^{1a}$, independently, is acetyl, $C_{1-6}$-alkyl, $C_{2-6}$-alkenyl, $C_{2-6}$-alkynyl, $C_{3-7}$-cycloalkyl, —$SC_{1-6}$-alkyl, —$OC_{1-6}$-alkyl, —$NHC_{1-6}$-alkyl, —$C(O)C_{1-6}$-alkyl, —$COOR^7$, —$C(O)NR^7R^7$, —$NR^7C(O)R^7$, —$NR^7C(O)NR^7R^7$, —$NR^7(COOR^7)$, —$S(O)_2R^7$, —$S(O)_2R^7$, —$S(O)_2NR^7R^7$, —$NR^7S(O)_2NR^7R^7$, —$NR^7S(O)_2R^7$ or a phenyl, pyridyl, pyrimidinyl, pyridazinyl, pyazinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl, cycloheptyl or pyranyl, said ring optionally substituted independently with 1-5 substituents of $R^7$;

each $R^5$, independently, is halo, haloalkyl, haloalkoxyl, CN, OH, SH, $NO_2$, $NH_2$, $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl or —$C(O)R^7$;

$R^6$ is $R^7$;

each $R^7$, independently, is H, halo, haloalkyl, haloalkoxyl, CN, OH, SH, $NO_2$, $NH_2$, acetyl, $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl, $SR^8$, $OR^8$, $NR^8R^8$, $C(O)R^8$, $COOR^8$, $C(O)NR^8R^8$, $NR^8C(O)R^8$, $NR^8C(O)NR^8R^8$, $NR^8$ $(COOR^8)$, $S(O)_2R^8$, $S(O)_2NR^8R^8$, $NR^8S(O)_2R^8$, $NR^8S(O)_2NR^8R^8$ or a ring selected from phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, wherein each of the $C_{1\text{-}10}$-alkyl, $C_{2\text{-}10}$-alkenyl, $C_{2\text{-}10}$-alkynyl, $C_{3\text{-}10}$-cycloalkyl, $C_{4\text{-}10}$-cycloalkenyl, $C_{1\text{-}10}$-alkylamino-, $C_{1\text{-}10}$-dialkylamino-, $C_{1\text{-}10}$-alkoxyl, $C_{1\text{-}10}$-thioalkoxyl and ring is optionally substituted independently with 1-5 substituents of halo, haloalkyl, haloalkoxyl, CN, $NO_2$, $NH_2$, OH, oxo, $C_{1\text{-}6}$alkyl, $C_{1\text{-}6}$alkoxyl, $C_{3\text{-}6}$cycloalkyl, $C_{1\text{-}10}$-alkylamino-, $C_{1\text{-}10}$-dialkylamino-, benzyl or phenyl; and n is 0, 1 or 2.

The many different embodiments for the various elements, chemical moieties or R or L groups described and defined hereinabove with respect to compounds of Formula I also apply, and are included herein, to compounds of Formula II, where appropriate, as appreciated by those of ordinary skill in the art.

In yet another embodiment, Formulas I and II include the exemplary compounds and solvates, tautomers and pharmaceutically acceptable salt forms thereof, intermediates related thereto, examples of which are described in the Examples herein. For example, and in another embodiment, the invention provides the following compounds, and pharmaceutically acceptable salt forms thereof, selected from: N-(4-(6,7-dimethoxyquinolin-4-yloxy)phenyl)-2-(4-fluorophenylamino)benzamide;

N-(4-(6,7-dimethoxyquinolin-4-yloxy)phenyl)-2-(phenylamino)benzamide;

N-(4-(6,7-dimethoxyquinolin-4-yloxy)phenyl)-2-(3-fluorophenylamino)benzamide;

5-fluoro-N-(4-(7-methoxy-1,5-naphthyridin-4-yloxy)phenyl)-2-(phenylamino)benzamide;

N-(4-(7-methoxy-1,5-naphthyridin-4-yloxy)phenyl)-2-(phenylamino)benzamide;

N-(3-fluoro-4-(7-methoxyquinolin-4-yloxy)phenyl)-2-(phenylamino)benzamide;

N-(4-(2-aminopyrimidin-4-yloxy)phenyl)-2-(4-fluorophenylamino)benzamide;

N-(4-(7-methoxy-1,5-naphthyridin-4-ylthio)phenyl)-2-(piperidin-1-ylamino)benzamide;

N-(4-(7-methoxy-1,5-naphthyridin-4-yloxy)phenyl)-2-(piperidin-1-ylamino)benzamide;

N-methyl-4-(4-(2-(phenylamino)benzamido)phenoxy)picolinamide; and

N-(4-(7-methoxy-1,5-naphthyridin-4-ylthio)phenyl)-2-(4-methoxypiperidin-1-ylamino)benzamide.

DEFINITIONS

The following definitions should further assist in understanding the scope of the invention described herein.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, non-small cell lung cancer, pancreatic cancer, cervical cancer, bladder cancer, hepatoma, breast cancer, colon cancer, and head and neck cancer. While the term "cancer" as used herein is not limited to any one specific form of the disease, it is believed that the compounds and related methods of the invention will be particularly effective for cancers which are found to be accompanied by unregulated levels of Aurora kinase(s) in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human.

A "pharmaceutically-acceptable derivative" denotes any salt (also referred to as "pharmaceutically-acceptable salt"), any prodrug such as a phospshate or an ester of a compound of this invention, or any other compound which upon administration to a patient is capable of providing (directly or indirectly) a compound of this invention, or a metabolite or residue thereof, characterized by the ability to inhibit Aurora kinase.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies.

The terms "ring" and "ring system" refer to a one or more rings, fused where more than one ring, comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is not fully unsaturated.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

Where the term "alkyl" is used, either alone or within other terms such as "haloalkyl" and "alkylamino", it embraces linear or branched radicals preferably having alpha to beta number of carbon atoms. For example a $C_1$-$C_{10}$ alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated.

The term "alkenyl", alone or in combination, embraces linear or branched radicals having at least one carbon-carbon double bond and having two or more carbon atoms. Examples of alkenyl radicals include, without limitation, ethenyl, propenyl, allyl, propenyl, butenyl and 4-methylbutenyl. The term "alkenyl" embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of alkynyl radicals include, without limitation, ethynyl, propynyl (propargyl), butynyl, and the like. It is contemplated herein that alkynyl radicals may be optionally substituted with various substituents, where indicated.

The term "halo", alone or in combination, means halogens such as fluorine (F), chlorine (Cl), bromine (Br) or iodine (I) atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "alkoxy", alone or in combination, embraces linear or branched oxy-containing radicals each having alkyl portions of alpha to beta number of carbon atoms. For example, a $C_{1-10}$ alkoxy radical indicates an alkoxide having one to ten carbon atoms, arranged in a linear or branched fashion, attached to an oxygen atom. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S" is intended to encompass those mono- or multicyclic rings wherein the moiety is chemically stable and may be isolated in nature. Thus, rings wherein —O—O— or —S—S— or —N—O—S— type linkages are not stable, as appreciated by persons of ordinary skill in the art, and not intended to be within the scope of the invention.

The term "partially or fully saturated" as used herein, refers to a moiety, linear, branched or cyclic in nature, having no atom-atom double or triple bonds (fully saturated) or having one or more atom-atom double or triple bonds which are arranged such that where the structural moiety is cyclic, the cycle is not fully unsaturated (non-aromatic), as appreciated by those skilled in the art.

The term "fully unsaturated" as used herein, refers to a moiety having double or triple bonds, arranged in a manner such that the structure is aromatic in nature, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 or more substituents such as lower alkyl, hydroxyl, halo, haloalkyl, nitro, cyano, alkoxy and lower alkylamino, and the like. Phenyl substituted with —O—$CH_2$—O— forms an aryl benzodioxolyl substituent. Aryl as used herein, implies a fully unsaturated ring.

The term "heterocycles" or "heterocyclic radicals", alone or in combination, embraces saturated, partially saturated and partially unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 or more substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated (or partially unsaturated) heterocyclyl radicals include dihydrothienyl, dihydropyranyl, dihydrofuryl and dihydrothiazolyl.

The term "heteroaryl" radicals, alone or in combination, embraces fully unsaturated heteroatom-containing ring radicals, where the heteroatoms may be selected from nitrogen, sulfur and oxygen. Examples of heteroaryl radicals include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The terms "heterocycle" and "heteroaryl" also embraces radicals which are fused/condensed with aryl radicals: unsaturated condensed heterocyclic or heteroaryl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b] pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially and fully saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The term "carbonyl", whether used alone or with other terms, such as "aminocarbonyl", denotes —(C=O)—.

The term "alkylthio" or "thioalkyl" embraces radicals containing a linear or branched alkyl radical, of one to ten carbon atoms, attached to a divalent sulfur atom. An example of "alkylthio" is methylthio, ($CH_3S$—).

The term "aminoalkyl" and "diaminoalkyl" embraces "N-alkylamino" and "N,N-dialkylamino", respectively, where amino groups are independently substituted with one alkyl radical and with two alkyl radicals, respectively. Examples of alkylamino radicals include "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "$C_{1-10}$alkyl-amino-" denotes amino groups, which have been substituted with one or two alkyl radicals, such as N-methylamino. The alkylamino radicals may be further substituted on the alkyl portion of the radical.

The term "aryl-alkyl-amino-" or "aralkylamino" denotes amino groups, which have been substituted with one or two aryl-substituted-alkyl radicals, such as benzyl-amino. The aralkyl-amino radicals may be further substituted on the aryl or alkyl portion of the radical.

The term "heterocyclyl-alkyl-amino-" denotes amino groups, which have been substituted with one or two heterocyclyl-substituted-alkyl radicals, such as piperidyl-methylamino. The heterocyclyl-alkyl-amino radicals may be further substituted on the heterocycle or alkyl portion of the radical.

The term "heteroaryl-alkyl-amino-" or "heteroaralkylamino" denotes amino groups, which have been substituted with one or two heteroaryl-substituted-alkyl radicals, such as pyrimidyl-amino. The heteroaralkyl-amino radicals may be further substituted on the heteroaryl or alkyl portion of the radical.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

The term "in conjunction with any of the above or below embodiments" is intended to mean that the invention further encompasses those compounds of Formulas I or II wherein various embodiments of variables $R^1$-$R^6$ and $L^1$ may be combined in with any other embodiment described herein with respect to $R^1$-$R^6$ and $L^1$.

The term "comprising" is meant to be open ended, including the indicated component(s) but not excluding other elements.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

The terms "Formula I" and "Formula II" include any sub formulas.

The present invention comprises processes for the preparation of a compound of Formulas I and II.

Also included in the family of compounds of Formulas I-II are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-II may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-II include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound of Formulas I-II. When a basic group and an acid group are present in the same molecule, a compound of Formulas I-II may also form internal salts.

General Synthetic Procedures

The compounds of the invention can be synthesized according to the following procedures of Schemes 1-4, wherein the substituents are as defined for Formulas I-II, above, except where further noted. The synthetic methods described below are merely exemplary, and the compounds of the invention may be synthesized by alternate routes as appreciated by persons of ordinary skill in the art.

The following list of abbreviations, used throughout the specification, represent the following:
ACN, AcCN, MeCN—acetonitrile
BSA—bovine serum albumin
$Cs_2CO_3$—cesium carbonate
$CHCl_3$—chloroform
$CH_2Cl_2$, DCM—dichloromethane, methylene chloride
DIBAL—diisobutylaluminum hydride
DIEA, DIPEA—diisopropylethylamine
DME—dimethoxyethane
DMF—dimethylformamide
DMAP—4-dimethylaminopyridine
DMSO—dimethylsulfoxide
dppa—diphenylphosphoryl azide
EDC—1-(3-dimethylaminopropyl)-3-ethylcarbodiimide hydrochloride
$Et_2O$—diethyl ether
EtOAc ethyl acetate
FBS—fetal bovine serum
g, gm—gram
h, hr—hour
HBr—hydrobromic acid
HCl—hydrochloric acid
HOBt—1-hydroxybenzotriazole hydrate
$H_2$—hydrogen
$H_2O_2$—hydrogen peroxide
HATU—O-(7-azabenzotriazol-1-yl)-N,N,N',N'-tetramethyluroniumhexafluorophosphate
HPLC—high pressure liquid chromatography
IPA, IpOH—isopropyl alcohol
$K_2CO_3$—potassium carbonate
MCPBA—meta-chloroperbenzoic acid
$MgSO_4$—magnesium sulfate
MeOH—methanol
$N_2$—nitrogen
$NaHCO_3$—sodium bicarbonate
NaOH—sodium hydroxide
NaH—sodium hydride
$Na_2SO_4$—sodium sulfate
$NH_4Cl$—ammonium chloride
$NH_4OH$—ammonium chloride
NMP—N-methylpyrrolidinone
$P(t-bu)_3$—tri(tert-butyl)phosphine
PBS—phospate buffered saline
Pd/C—palladium on carbon
$Pd(PPh_3)_4$—palladium(0)triphenylphosphine tetrakis
$Pd(PhCN)_2Cl_2$—palladium di-cyanophenyl dichloride
$Pd(OAc)_2$—palladium acetate
$Pd_2(dba)_3$—bis(dibenzylideneacetone) palladium
PyBop—benzotriazol-1-yl-oxy-tripyrrolidino-phosphonium hexafluorophosphate
RT, rt—room temperature
RBF—round bottom flask
rac-BINAP—2,2'-Bis(diphenylphosphine)-1,1'-binaphthyl
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran

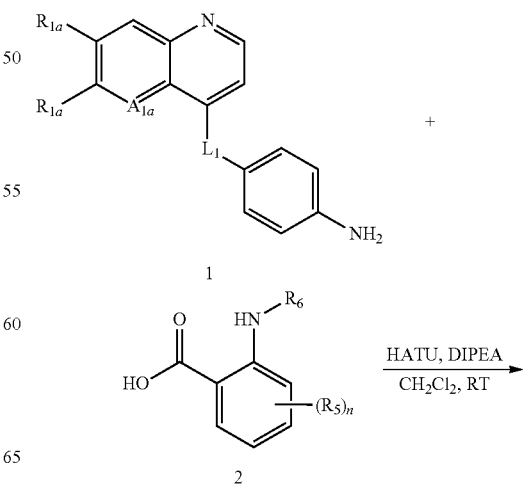

Scheme 1 (Method A)

-continued

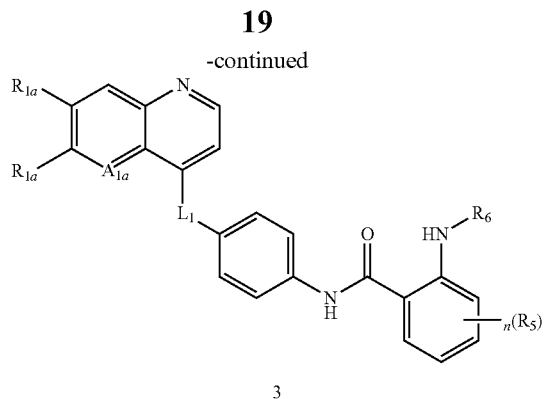

3

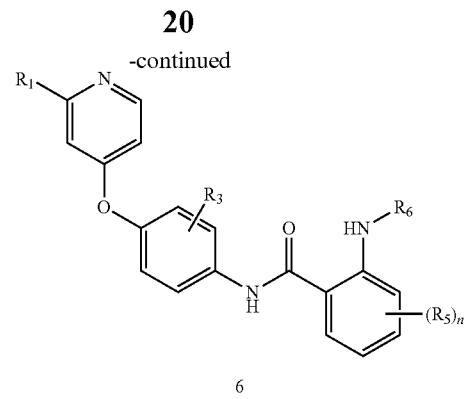

6

Compounds 3 of Formula II (as shown above), can be prepared according to the method generally described in Scheme 1. As shown, activation of the carboxylic acid group of compound 2 with a suitable activating group, such as the HATU ester as shown, followed by displacement with the amine nucleophile of compound 1 (in the presence of a suitable solvent, such as DCM, and a suitable base) should generally afford the final target compound 3. Note that HATU is a known agent which activates carboxylic acids to esters, which then can be displaced by nucleophilic species, such as amines. Other suitable acid activating agents, including HBTU, TATU, TBTU, carbodiimides, and the like may be used. Alternatively, the acid OH group may be converted or activated to the corresponding acid halide, such as an acid chloride or acid fluoride with known methods, such as oxalyl chloride for the acid chloride. Such activation to activated esters or halides are characterized herein as "leaving groups" or "LG" for short. In addition, heat may or may not be necessary to drive the reaction to completion or to obtain improved yields. It should be understood that compound 3 may also be a compound of formula I as described herein. Representative examples of such reactions are further described below.

The strategy for preparing compounds 3, as exemplified in scheme 1, may generally be approached by building and/or breaking down 2 primary linking bonds, i.e., the connections of both $L^1$ and —$NR^4$—. Thus, compounds 6 (similar to compounds 3 but having $A^{3-6}$ as carbon atoms to form a phenyl ring, as in Formula I herein) may be prepared according to the method shown in scheme 2 below.

Compounds 6 of Formulas I-II (where $L^1$ is O, $A^1$ and $A^2$ are each CH and $A^{3-6}$ are each $CR^3$), can be prepared according to the method generally described in Scheme 2. As shown, a nucleophilic displacement reaction, under basic conditions with irradiation, by a compound 5 of an aryl halide 4 (where the halide as shown is chloride) should generally afford ether linked $L^1$ compounds 6. Suitable bases to yield compound 6 include, without limitation, carbonate bases such as cesium carbonate ($Cs_2CO_3$; shown above), $Na_2CO_3$, $K_2CO_3$ and the like in a suitable solvent, whose properties will generally depend upon the solubility of the starting materials, polarity, and other factors readily appreciated in the art.

In scheme 2, compound 5 may also be a thiol (which is not shown) to effect the transformation to compound 6, as appreciated by those skilled in the art.

The strategy for preparing compounds 3, as exemplified in scheme 1, may generally be approached by building and/or breaking down 2 primary linking bonds, i.e., the connections of both $L^1$ and —$NR^4$—. Thus, compounds 6 (similar to compounds 3 but having $A^{3-6}$ as carbon atoms to form a phenyl ring, as in Formula I herein) may be prepared according to the method shown in scheme 2 below.

Scheme 2 (Method B-1)

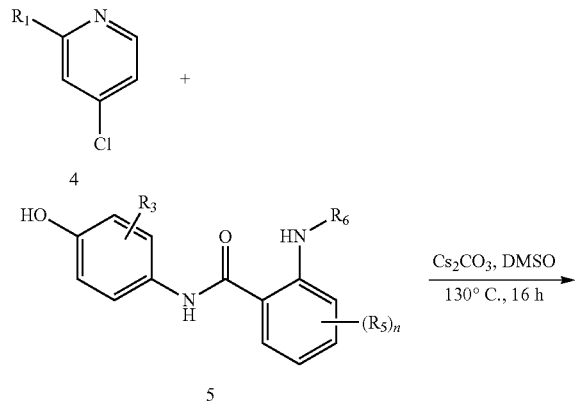

Scheme 2 (Method B-1)

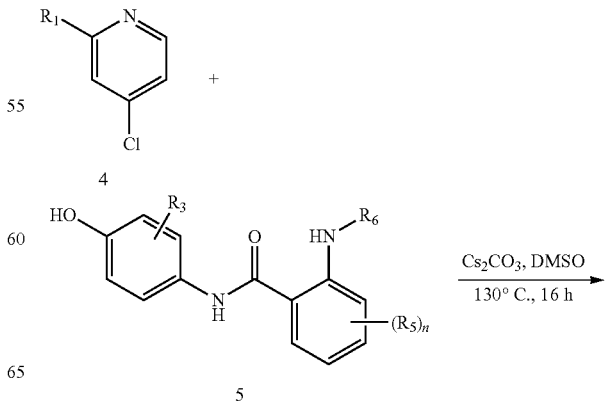

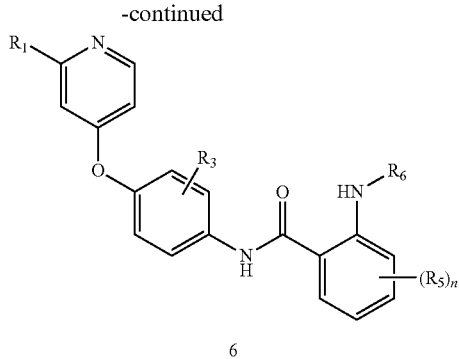

6

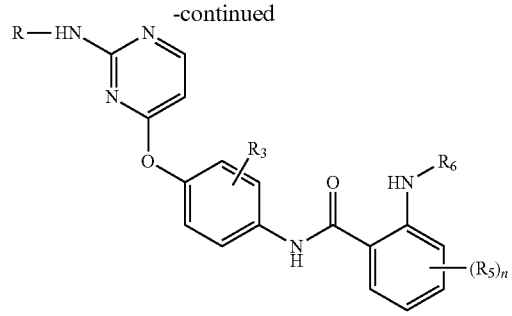

9

Compounds 6 of Formulas I-II (where L1 is O, A1 and A2 are each CH and A3-6 are each CR3), can be prepared according to the method generally described in Scheme 2. As shown, a nucleophilic displacement reaction, under basic conditions with irradiation, by a compound 5 of an aryl halide 4 (where the halide as shown is chloride) should generally afford ether linked L1 compounds 6. Suitable bases to yield compound 6 include, without limitation, carbonate bases such as cesium carbonate (Cs2CO3; shown above), Na2CO3, K2CO3 and the like in a suitable solvent, whose properties will generally depend upon the solubility of the starting materials, polarity, and other factors readily appreciated in the art.

In scheme 2, compound 5 may also be a thiol (which is not shown) to effect the transformation to compound 6, as appreciated by those skilled in the art. Where compound 5 is a thiol, the reaction may be accomplished without the need for acidic or basic conditions, and may also be accomplished at ambient temperatures, as appreciated by those skilled in the art. Representative examples of such reactions are further described hereinbelow. Suitable transformation methods are known to those skilled in the art, and are generally described in Jerry March's Advanced Organic Chemistry, 4$^{th}$ edition (1992), which disclosure is hereby incorporated by reference in its entirety.

Scheme 3 (Method B-2)

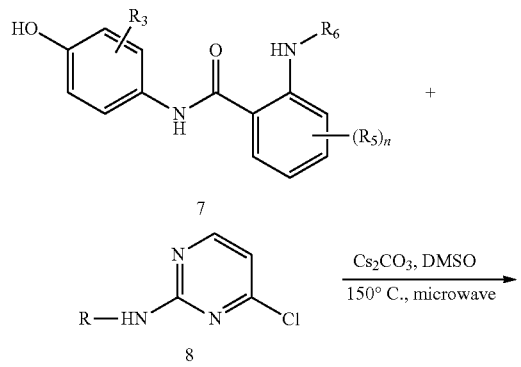

Compounds 9 (wherein R$^1$ is a unsubstituted or substituted amine) can be made by reacting alcohol compounds 7 (where L$^1$ is —O—) with chloro-pyrimidines 8 under suitable conditions, such as those described in scheme 3 above, to afford the desired product 9. Note that any protecting groups on the amine may be necessary, which protecting group can be removed or functional group can be deprotected after the reaction is complete.

The following Examples represent exemplary methods of synthesizing or preparing desired compounds of Formulas I-II, intermediates and various starting materials and/or building blocks thereof. It should be appreciated that these methods are merely representative examples and other conventional, known or developed alternative methods may also be utilized. It should also be appreciated that the exemplary compounds are merely for illustrative purposes only and are not to be construed as limiting the scope of the present invention in any manner.

Analytical Methods:

Unless otherwise indicated, all HPLC analyses were run on a Agilent Model 1100 system with an Agilent Technologies Zorbax SB-C$_8$ (5μ) reverse phase column (4.6×150 mm; Part no. 883975-906) run at 30° C. with a flow rate of about 1.50 mL/min. The mobile phase used solvent A (H$_2$O/0.1% TFA) and solvent B (AcCN/0.1% TFA) with a 11 min gradient from 5% to 100% AcCN. The gradient was followed by a 2 min return to 5% AcCN and about a 2.5 minute re-equilibration (flush).

LC-MS Method:

Samples were run on a Agilent model-1100 LC-MSD system with an Agilent Technologies XDB-C$_8$ (3.5μ) reverse phase column (4.6×75 mm) at 30° C. The flow rate was constant and ranged from about 0.75 mL/min to about 1.0 mL/min.

The mobile phase used a mixture of solvent A (H$_2$O/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation with a 30×50 mm column at 40 mL/min. The mobile phase used a mixture of solvent A (H$_2$O/0.1% TFA) and solvent B (AcCN/0.1% TFA) with a 15 min gradient from 10% to 95% solvent B. The gradient is followed by a 2 min return to 10% AcCN.

Proton NMR Spectra:

Unless otherwise indicated, all $^1$H NMR spectra were run on a Varian series Mercury 300 MHz or on a Bruker 400 MHz instrument. Where so characterized, all observed protons are reported as parts-per-million (ppm) downfield from tetramethylsilane (TMS) or other internal reference in the appropriate solvent indicated.

Example 1

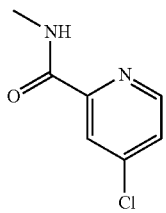

4-Chloro-N-methylpicolinamide

The titled compound was prepared according to a method described in Bankston, D et. al., *Org. Proc. Res. Dev.* 2002, 6, 777-781.

Example 2

8-Chloro-3-methoxy-1,5-naphthyridine

The titled compound was prepared according to a method described in. pgs 47-50 in co-pending U.S. patent application Ser. No. 12/080,669, which pages are hereby incorporated herein by reference.

Example 3

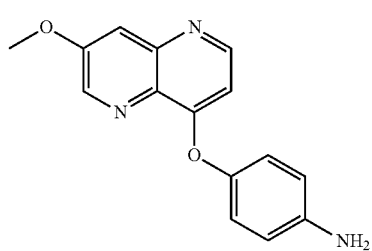 [SMILES: COc1cnc2c(Oc3ccc(N)cc3)ccnc2c1]

4-(7-Methoxy-1,5-naphthyridin-4-yloxy)benzenamine

The titled compound was prepared according to a method described in. pgs 57-58 in co-pending U.S. patent application Ser. No. 12/080,669, which pages are hereby incorporated herein by reference.

Example 4

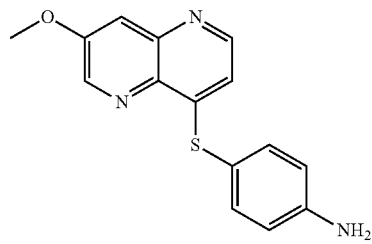 [SMILES: COc1cnc2c(Sc3ccc(N)cc3)ccnc2c1]

4-(7-Methoxy-1,5-naphthyridin-4-ylthio)benzenamine

The titled compound was prepared according to a method described in. pg. 58 in co-pending U.S. patent application Ser. No. 12/080,669, which pages are hereby incorporated herein by reference.

Example 5

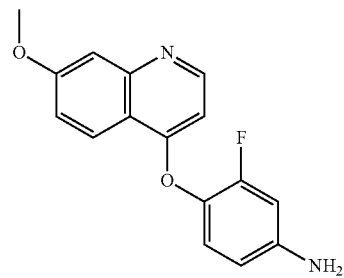 [SMILES: COc1ccc2c(Oc3ccc(N)cc3F)ccnc2c1]

3-Fluoro-4-(7-methoxyquinolin-4-yloxy)benzenamine

Step 1:

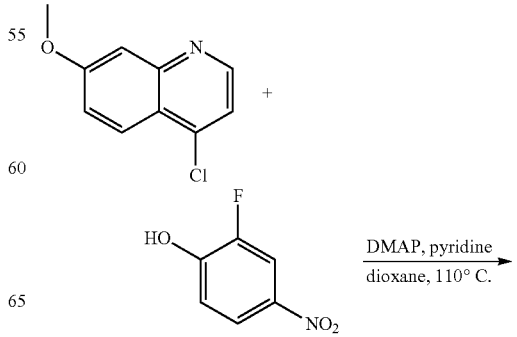

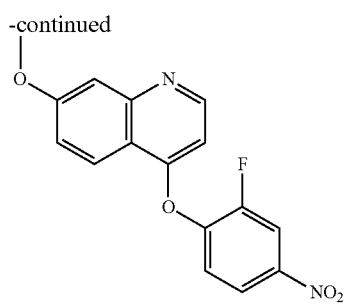

To 4-chloro-7-methoxyquinoline (0.900 g, 4.6 mmol), 2-fluoro-4-nitrophenol (2.3 g, 14 mmol), and N,N-dimethylpyridin-4-amine (0.068 g, 0.56 mmol) was added dioxane (10 mL) and pyridine (6.4 ml, 79 mmol). The resulting mixture was heated at 110° C. in an argon-purged sealed tube for 16 hours. An aliquot was analyzed by LCMS and indicated the presence of desired product. The reaction mixture was concentrated in vacuo and diluted with 2 N NaOH. The resulting solid was filtered, and the filtrate was extracted with CH$_2$Cl$_2$. The organic layers were dried over sodium sulfate and filtered through a pad of silica gel along with the solids using 10% MeOH/CH$_2$Cl$_2$ as eluent. The collected fractions were concentrated in vacuo to yield 4-(2-fluoro-4-nitrophenoxy)-7-methoxyquinoline (0.900 g, 2.3 mmol, 49% yield) as a brownish solid. Calcd for C$_{16}$H$_{11}$FN$_2$O$_4$: [M]$^+$=314. Found: [M+H]$^+$=315.

Step 2

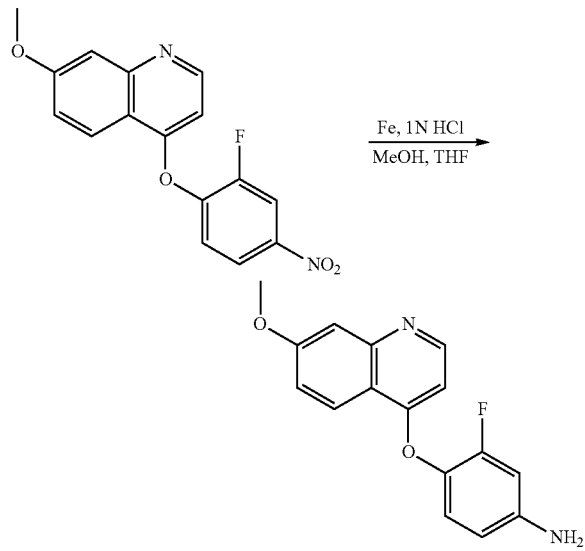

To 4-(2-fluoro-4-nitrophenoxy)-7-methoxyquinoline (0.900 g, 2.9 mmol) in THF was added methanol (53 ml, 1297 mmol) and 1N HCl (8.6 ml, 8.6 mmol). The resulting mixture was cooled to 0° C. Iron (2.2 g, 40 mmol) was added, and the reaction was allowed to stir at RT for 3.5 hours. The reaction mixture was then diluted with MeOH, filtered through a pad of Celite, and concentrated in vacuo. The residue was then diluted with sat. NaHCO$_{3\ (aq)}$ and CH$_2$Cl$_2$. The aqueous layer was separated and extracted three times with CH$_2$Cl$_2$. The combined organic extracts were dried over sodium sulfate and filtered through a pad of silica gel using 10% MeOH/CH$_2$Cl$_2$. The collected fractions were concentrated in vacuo and purified by silica gel chromatography (80 g column; 2% MeOH/CH$_2$Cl$_2$ for 10 minutes then 3.5% MeOH/CH$_2$Cl$_2$ for 10 minutes). Fractions containing pure product were concentrated to yield 3-fluoro-4-(7-methoxyquinolin-4-yloxy)benzenamine as a tan solid. Calcd for C$_{16}$H$_{13}$FN$_2$O$_2$: [M]$^+$=284. Found: [M+H]$^+$=285.

Example 6

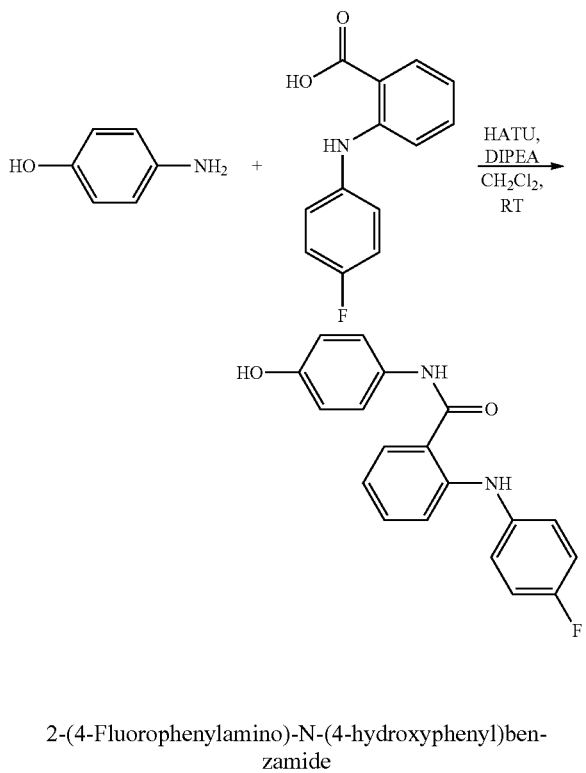

2-(4-Fluorophenylamino)-N-(4-hydroxyphenyl)benzamide

In a 100-mL RBF was combined 2-(4-fluorophenylamino)benzoic acid (2.5 g, 11 mmol), HATU (4.9 g, 13 mmol), 4-aminophenol (1.0 g, 9.2 mmol), N-ethyl-N-isopropylpropan-2-amine (3.2 mL, 18 mmol), and DCM (23 mL, 9.2 mmol). The reaction mixture was allowed to stir at RT overnight and was then absorbed onto a loading cartridge and passed through an 80 g silica gel column using hexanes: EtOAc as eluent. Fractions containing pure product were concentrated in vacuo to afford 2-(4-fluorophenylamino)-N-(4-hydroxyphenyl)benzamide as a brown oil. The oil was triturated with CH$_2$Cl$_2$ and hexanes, and the resulting solid was filtered through a 0.45 μM membrane filter and rinsed with hexanes. 2-(4-fluorophenylamino)-N-(4-hydroxyphenyl)benzamide was isolated as a off-white solid. Calcd for $C_{19}H_{15}FN_2O_2$: $[M]^+$=322. Found: $[M+H]^+$=323.

Example 7

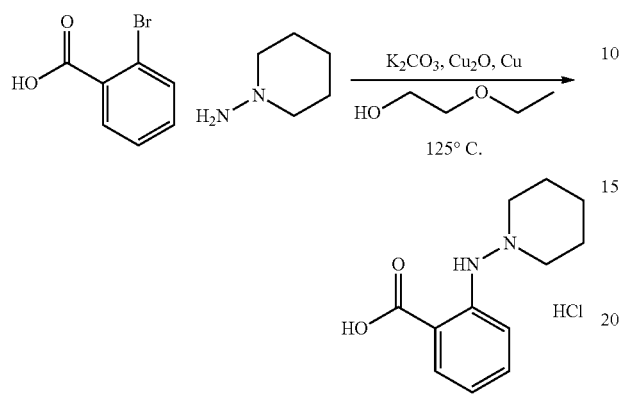

2-(Piperidin-1-ylamino)benzoic acid hydrochloride

Piperidin-1-amine (0.96 g, 9.6 mmol), 2-bromobenzoic acid (1.75 g, 8.7 mmol), copper powder (0.055 g, 0.87 mmol), potassium carbonate (1.2 g, 8.7 mmol), and copper oxide (0.062 g, 0.44 mmol), and 2-ethoxyethanol were combined in a sealed tube and heated at 125° C. overnight. The reaction mixture was then diluted with 25 mL of water and filtered through charcoal. The mixture was then acidified with 1 N HCl and concentrated in vacuo to afford 2.2 g of crude product. Calcd for $C_{12}H_{16}N_2O_2$: $[M]^+$=220. Found: $[M+H]^+$=221.

Example 8

Analogous to Method A

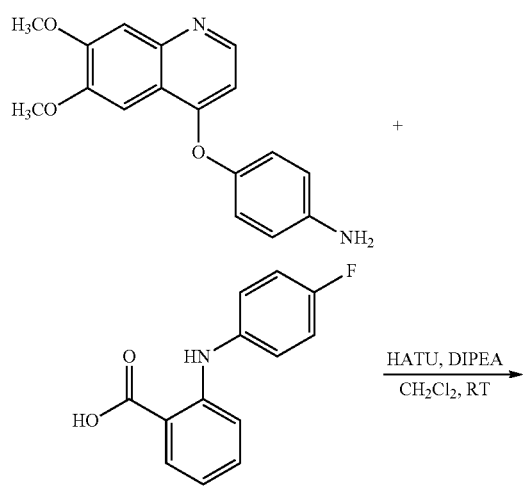

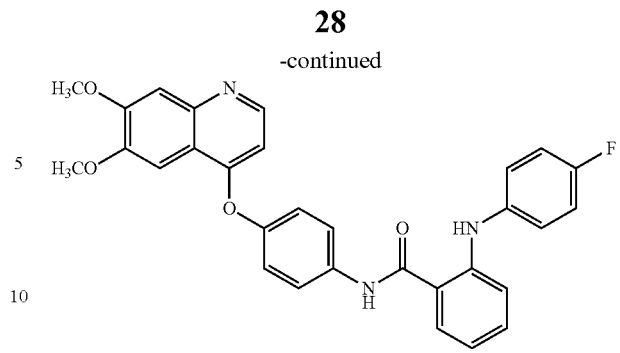

N-(4-(6,7-Dimethoxyquinolin-4-yloxy)phenyl)-2-(4-fluorophenylamino)benzamide 4-(6,7-Dimethoxyquinolin-4-yloxy)benzenamine (60 mg, 202 μmol), 2-(4-fluorophenylamino)benzoic acid (56 mg, 243 μmol), and HATU (108 mg, 283 μmol) were combined in a resealable tube. DCM (1012 μl, 202 μmol) and N-ethyl-N-isopropylpropan-2-amine (71 μl, 405 μmol) were added, and the reaction mixture in the tube was allowed to stir at RT. Upon completion (as judged by LCMS), the reaction mixture was concentrated in vacuo, dissolved in minimal DMSO and purified by preparative HPLC {15-85% (0.1% TFA in $CH_3CN$) in $H_2O$ over 20 min}. Fractions containing pure product were combined and neutralized with saturated aqueous $NaHCO_3$ then extracted with EtOAc, dried over $MgSO_4$, filtered, and concentrated in vacuo to afford pure N-(4-(6,7-dimethoxyquinolin-4-yloxy)phenyl)-2-(4-fluorophenylamino)benzamide as a off-white solid. MS Calcd for $C_{30}H_{24}FN_3O_4$: $[M]^+$=509. Found: $[M+H]^+$=510.

Example 9

Analogous to Method B-1

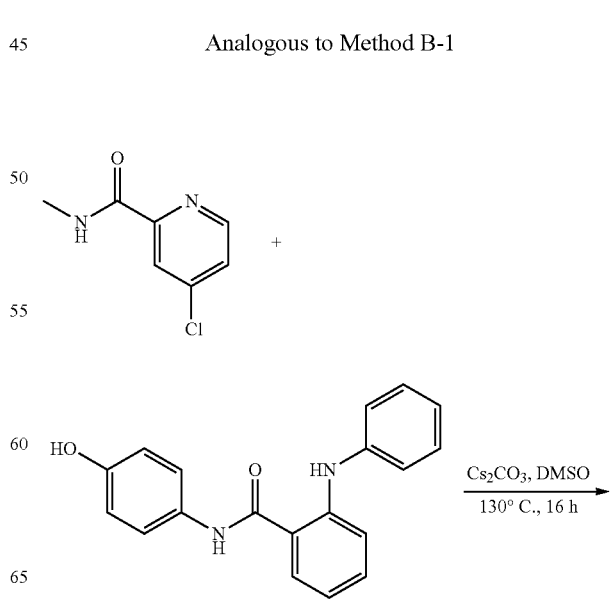

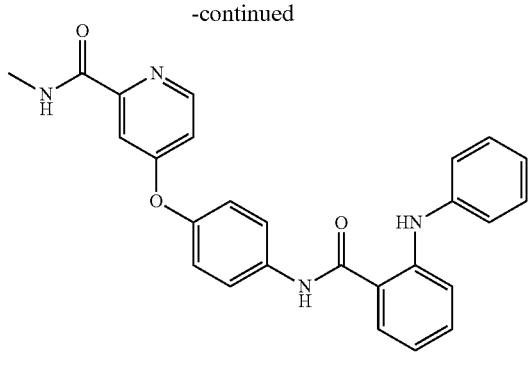

N-Methyl-4-(4-(2-(phenylamino)benzamido)phenoxy)picolinamide

4-Chloro-N-methylpicolinamide (70 mg, 410 μmol), N-(4-hydroxyphenyl)-2-(phenylamino)benzamide (150 mg, 492 μmol), cesium carbonate (267 mg, 821 μmol), and DMSO (410 μl 410 μmol) were added into a screw-capped test tube. The tube was sealed and placed in a preheated oil bath at 130° C. After 16 h, LC-MS showed mainly desired product. Water was added, and a gray solid precipitated out of the solution. The solid was filtered off and rinsed with water. The product was purified by reverse phase preparative HPLC. Fractions containing the product were combined, neutralized with sat NaHCO$_3$ $_{(aq)}$, washed with brine, dried over MgSO$_4$, and concentrated in vacuo. The product, N-methyl-4-(4-(2-(phenylamino)benzamido)phenoxy)picolinamide was collected as a black solid. MS Calcd for C$_{26}$H$_{22}$N$_4$O$_3$: [M]$^+$=438. Found: [M+H]$^+$=439.

Example 10

Analogous to Method B-2

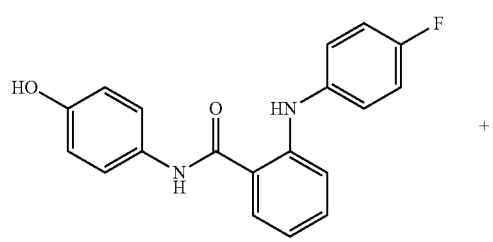

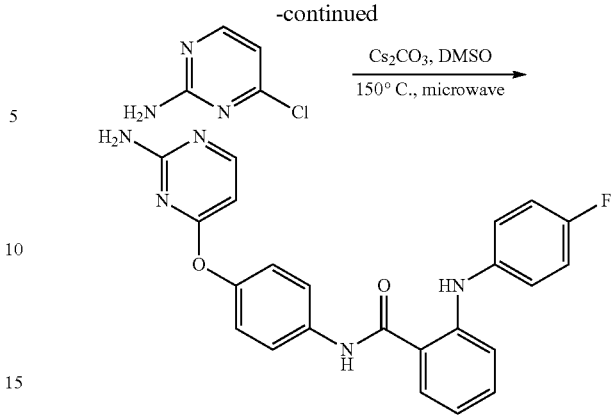

N-(4-(2-aminopyrimidin-4-yloxy)phenyl)-2-(4-fluorophenylamino)benzamide

A mixture of 2-(4-fluorophenylamino)-N-(4-hydroxyphenyl)benzamide (157 mg, 486 μmol), 2-amino-4-chloropyrimidine (60 mg, 463 μmol), and cesium carbonate (302 mg, 926 μmol) in DMSO (2316 μl, 463 μmol) was placed in a microwave pressure vial, the vial was sealed, and the vial (reaction mixture) was heated in a Biotage Microwave to 150° C. for 12 minutes. LCMS analysis indicated that the reaction was complete. Reaction was diluted with EtOAc and washed with sat NaHCO$_3$ $_{(aq)}$. The organic layer was dried over sodium sulfate and concentrated in vacuo to give a brown color oil. The oil was taken up in minimal amount of DMSO and purified by Gilson HPLC {10-80% (0.1% TFA in CH$_3$CN) in H$_2$O over 20 min} to afford pure N-(4-(2-aminopyrimidin-4-yloxy)phenyl)-2-(4-fluorophenylamino)benzamide. MS Calcd for C$_{23}$H$_{18}$FN$_5$O$_2$=415. Found: [M+H]$^+$=416.

The Examples disclosed in Table I below are additional exemplary compounds, of the present invention. These compounds were named in accordance to the naming convention commensurate with ACD and ChemDraw software version 8 (IUPAC naming convention). The compounds were made by the methods indicated in Table I, which generally correlate to the methods described in Schemes 1-3 and more specifically in Examples 8-10, respectively. The MS data measured for each compound is the M+H$^+$ ion value found for that compound. Biological data, where measured, is provided for the compounds in Table I.

TABLE I

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 11 | N-(4-(6,7-dimethoxyquinolin-4-yloxy)phenyl)-2-(4-fluorophenylamino)benzamide | 510.1 | A | ++++ | ++++ | ++++ |
| 12 | N-(4-(6,7-dimethoxyquinolin-4-yloxy)phenyl)-2-(phenylamino)benzamide | 492.3 | A | ++++ | ++++ | ++++ |
| 13 | N-(4-(6,7-dimethoxyquinolin-4-yloxy)phenyl)-2-(3-fluorophenylamino)benzamide | 510.1 | A | ++++ | ++++ | ++++ |
| 14 | 5-fluoro-N-(4-(7-methoxy-1,5-naphthyridin-4-yloxy)phenyl)-2-(phenylamino)benzamide | 481 | A | ++++ | ++++ | ++++ |

TABLE I-continued

| Ex. No. | Name | MS Data | Method | AurA_IC50_IP (uM Avg) | AurB_IC50_IP (uM Avg) | 24h_4N Ploidy EC50_IP (uM Avg) |
|---|---|---|---|---|---|---|
| 15 | N-(4-(7-methoxy-1,5-naphthyridin-4-yloxy)phenyl)-2-(phenylamino)benzamide | 463.1 | A | ++++ | ++++ | ++++ |
| 16 | N-(4-(6,7-dimethoxyquinolin-4-yloxy)-3-fluorophenyl)-2-(phenylamino)benzamide | 510.4 | A | ++++ | ++++ | |
| 17 | N-(3-fluoro-4-(7-methoxyquinolin-4-yloxy)phenyl)-2-(phenylamino)benzamide | 480.2 | A | ++++ | ++++ | +++ |
| 18 | N-(4-(2-aminopyrimidin-4-yloxy)phenyl)-2-(4-fluorophenylamino)benzamide | 416 | B2 | +++ | +++ | + |
| 19 | N-(4-(7-methoxy-1,5-naphthyridin-4-ylthio)phenyl)-2-(piperidin-1-ylamino)benzamide | 486.2 | A | ++ | ++++ | ++ |
| 20 | N-(4-(7-methoxy-1,5-naphthyridin-4-yloxy)phenyl)-2-(piperidin-1-ylamino)benzamide | 470.2 | A | ++ | +++ | + |
| 21 | N-methyl-4-(4-(2-(phenylamino)benzamido)phenoxy)picolinamide | 439 | B1 | + | +++ | + |
| 22 | N-(4-(7-methoxy-1,5-naphthyridin-4-ylthio)phenyl)-2-(4-methoxypiperidin-1-ylamino)benzamide | 516.2 | A | + | ++++ | ++ |

The invention further provides methods for making compounds of Formulas I-II. For example, and in one embodiment, there is provided a method of making a compound of Formula 1, the method comprising the step of reacting compound of Formula A

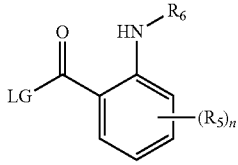

with a compound of Formula B

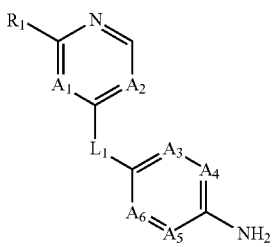

wherein R5, R6 and n of the compound of formula A and A1, A2, L1, R1 and A3-6 of the compound of formula B are as defined herein, and LG is a suitable leaving group, such as an activated carboxylate (HATU, TATU, TBTU ester) or a halide (acid chloride or fluoride), to make a compound of Formula I.

This method may also be used to make a compound of Formula II. In another embodiment, there is provided a method of making a compound of Formula II, the method comprising the step of reacting compound of Formula A

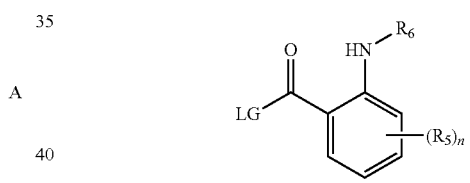

with a compound of Formula B

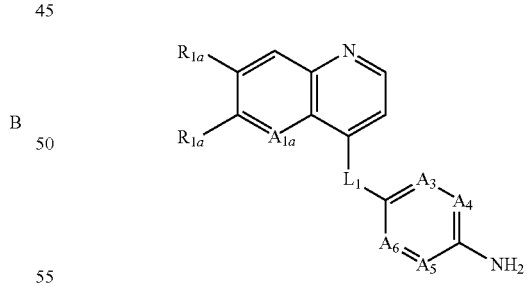

wherein $R^5$, $R^6$ and n of the compound of formula A and $A^{1a}$, $L^1$, $R^{1a}$ and $A^{3-6}$ of the compound of formula B are as defined herein, and LG is a suitable leaving group, such as an activated carboxylate (HATU, TATU, TBTU ester) or a halide (acid chloride or fluoride), to make a compound of Formula I.

While the examples described above provide processes for synthesizing compounds of Formulas I-II, other methods may be utilized to prepare such compounds. In the procedures described herein, the steps may be performed in an alternate order and may be preceded, or followed, by additional protection/deprotection steps as necessary.

Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jescheit, Aminosauren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide and Derivate (Chemistry of Carbohydrates: Monosaccharides and Derivatives), Georg Thieme Verlag, Stuttgart (1974).

The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like, many of which were utilized in the Examples above. Reactions conditions such as temperature, duration, pressure, and atmosphere (inert gas, ambient) are known in the art and may be adjusted as appropriate for the reaction.

All synthetic procedures described herein can be carried out either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further includes salt forms of compounds of Formulas I and II. Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

The invention further encompasses pro-drugs of compounds of Formulas I and II. For example, a phosphate group may be a pro-drug derivative of an alcohol group or an amine group, or an ester may be a pro-drug of a carboxylic acid functional group. Phosphate groups may be incorporated into desired compounds of Formulas I and II in order to improve upon in-vivo bioavailability and/or other pharmacokinetic (pK) or pharmacodynamic (PD) properties of the compound.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with chiral reagents, such as an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The synthetic chemistry transformations, as well as protecting group methodologies (protection and deprotection) described above and useful in synthesizing the inhibitor compounds described herein, are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Biological Evaluation

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I-II) vary with structural change, in general, activity possessed by compounds of Formulas I-II may be demonstrated both in vitro as well as in vivo. The following exemplified pharmacological assays have been carried out with compounds according to the invention. Briefly, representative compounds of the invention were found to inhibit the activity of Aurora kinase selectively or non-selectively, at doses less than 25 µM. This activity demonstrates the utility of the compounds in the prophylaxis and treatment of cellular proliferative disorders, including cancer as described herein.

Aurora Kinase HTRF Assays

AuroraA-TPX2-Homogeneous Time Resolved Fluorescent (HTRF) Kinase Assay

The Aurora-A HTRF assay begins with Aurora-A in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The AuroraA HTRF assay comprises 1 µL of compound in 100% DMSO, 20 µL of ATP and biotinylated PLK, and 20 µL of AuroraA-TPX2 KD GST for a final volume of about 41 µL. The final concentration of PLK is about 1 µM. The final concentration of ATP is about 1 µM (Km(app)=1 µM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

Many of the Examples described herein were tested and found to be active compounds. Table I includes related biological data, which may be interpreted using the activity gauge below. Examples 25-44 exhibited an average activity in the Aurora kinase A HTRF assay as follows:

"+" represents an activity (average $IC_{50}$) in the range of 1.0 uM-5.0 uM;
"++" represents an activity (average $IC_{50}$) in the range of 500 nM-less than 1.0 uM;
"+++" represents an activity (average $IC_{50}$) in the range of 100-less than 500 nM; and
"++++" represents an activity (average $IC_{50}$) of less than 100 nM.

AuroraB-Homogeneous Time Resolved Fluorescent (HTRF) Kinase Assay:

The AuroraB HTRF assay begins with AuroraB in the presence of ATP phosphorylating the biotinylated peptide Histone H3. The reaction incubates for about 90 min. the reaction is quenched by addition of detection reagents, which stop the reaction by diluting out the enzyme and chelating the metals due to the presence of EDTA. After addition, the assay is incubated for about 60 min to allow detection reagents to equilibrate.

The AuroraB HTRF assay comprises 1 µL of compound in 100% DMSO, 20 µL of ATP and biotinylated Histone H3, and 20 µL of AuroraB FL His for a final volume of 41 µL. The final concentration of Histone H3 is 0.1 µM. The final concentration of ATP is 23 µM (Km(app)=23 µM+/−2.6) and the final concentration of AuroraB is 400 pM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-His H3) at a final conc of 0.064 nM.

The assay plate is read in either a Discovery or a RubyStar. The eu-anti-His H3 is excited at 320 nm and emits at 615 nm to excite the SA-APC which in turn emits at 655 nm. The ratio of SA-APC at 655 nm (excited due to close proximity to the Eu-anti-H is H3 because of phosphorylation of the peptide) to free Eu-anti-His H3 at 615 nm will give substrate phosphorylation.

Many of the Examples described herein were tested, and fund to be active compounds. Table I includes related biological data, which may be interpreted using the activity gauge below. Selected Examples 29-45 and 74-370 exhibited an average activity in the Aurora kinase B HTRF assay as follows:

"+" represents an activity (average $IC_{50}$) in the range of 1.0 uM-5.0 uM;
"++" represents an activity (average $IC_{50}$) in the range of 500 nM-less than 1.0 uM;
"+++" represents an activity (average $IC_{50}$) in the range of 100-less than 500 nM; and
"++++" represents an activity (average $IC_{50}$) of less than 100 nM.

Aurora Kinase Cell-Based Assay

HeLa Cell 24 hr Ploidy Assay Protocol

The purpose of this assay is to evaluate the ability of selected individual compounds to induce Deoxyribonucleic acid (DNA) content (ploidy) in cells through failed cell division. Cell cycle analysis is a rapid and efficient way to evaluate the status of DNA content (ploidy) of a given cell. HeLa cells ($1\times10^4$ HeLa cells/well) in 100 ul of media (MEM+10% FBS) were plated in 96-well plates (Packard View) and cultured for 24 hrs at 37° C. maintained in a 5% $CO_2$ atmosphere. The following day, cells were treated for 24 hrs with inhibitor compounds (10 pt. Dose ranging from 0.0024-1.25 umol/L). The compounds were serially diluted in DMSO (0.25% final concentration). The cells were fixed (3.7% Formaldehyde and 1% glutaraldehyde) and permeabilized (1×PBS with 1% BSA and 0.2% Triton X-100) in preparation for nuclear staining. The well plates were stained for 45 minutes at RT in the dark using Hoechest 33342 nuclear stain at 0.5 ug·ml (Stock of 10 mg/ml, Invitrogen, CA, Cat # H3570). The nuclear stain was removed by aspiration and the cells were washed with wash buffer. A Cellomics Array Scan Vti plate reader was used to acquire the DNA ploidy data of the cells using Cell Cycle bioapplication. Numbers for each of "valid cell count/well", "% of 4N cells" and "% of >4Ncells" were calculated with the assistance of an Activity Base 5.1ca software and dose curves were generated using an XLFit software. With XLFit, final $EC_{50}$ IP and $EC_{50}$ transit values, as well as the Max and Min, were calculated for each curve.

Of the compounds assayed, a number of compounds exhibited activity in the 24 h cell-ploidy content assay, as provided in the Tables herein. Selected Examples exhibited an average activity in the DNA ploidy assay as follows:

"+" represents an activity (average $IC_{50}$) in the range of 1.0 uM-5.0 uM;
"++" represents an activity (average $IC_{50}$) in the range of 500 nM-less than 1.0 uM;
"+++" represents an activity (average $IC_{50}$) in the range of 100-less than 500 nM; and
"++++" represents an activity (average $IC_{50}$) of less than 100 nM.

HCT116 Xenograft Model

Compounds of the present invention were evaluated in HCT116 xenografts, a human colon carcinoma model. HCT116 cells were chosen to evaluate compounds of Formulas I-II in a tumor model based on in vitro data having showed a marked increase in polyploidy in the cells in response to Aurora B inhibition. These cells were grown as subcutaneous xenografts in female HSD (Harlan Sprague Dawley) athymic nude mice. Mice were implanted subcutaneously with $2\times10^6$ cells in matrigel on day 0. Treatment was initiated on day 10 with compounds of the invention at the indicated dosage p.o for 2 consecutive-days per week (intermittent schedule, such as 2 days on-5 days off) or 7-days (continuous schedule) per week, for a selected number of weeks. For example, in one study, animals were dosed with selected compound samples BID on an intermittent dosing paradigm of two days on and then 5 days off per week, for four weeks (four dosing cycles)

at 15, 7.5, and 3.75 mg/kg. Tumor growth inhibition and body weights were measured throughout the study and compared to the vehicle control group. All groups were provided nutritional supplements on a daily basis throughout the study to maintain body weight. Terminal neutrophil counts were taken at the end of this study. Measures were made by ANOVA followed by Scheffe post hoc test using StatView software v5.0.1.

Materials

Tissue Culture:

10 Flasks containing a total of $7.68 \times 10^8$ HCT 116 tumor cells were harvested for tumor cell implantation. HCT 116 cells were re-suspended to a cell concentration of about $2 \times 10^7$ cells/ml in serum-free McCoys 5A media+50% matrigel. Cell viability was measured to be about 99.3%.

Animals:

Female Athymic Nude mice approximately 14 weeks of age (Harlan Sprague Dawley) were used for the experiment. Mice were housed five per filter-capped cage in sterile housing in an environmentally controlled room (temperature 23±2° C., relative humidity 50±20%) on a 12-hr light/dark cycle. Animals were fed a commercial rodent chow (Formulation 8640; Tek Lab, Madison, Wis.) and received filter-purified tap water ad libitum. Dietary calcium and phosphorus contents were 1.2% and 1.0%, respectively. Mice were individually identified by microchips (Biomedic Data Systems, Inc—Seaford, Del.) implanted subcutaneously at least one week prior to the study. Mice were implanted with $2 \times 10^6$ cells (100 µl) subcutaneously on the right flank on Day 0. On Day 9, tumor-bearing mice were measured and randomized into five groups (n=10). Treatment of the mice with various compound dosages began on Day 10. The duration of the dosing phase of the study was generally four weeks. During the dosing period, mouse tumor volumes were measured with a digital caliper and weighed twice per week. Tumor volumes were calculated as follows: Tumor Volume $(mm^3) = [(W^2 \times L)/2]$ where width (W) is defined as the smaller of the 2 measurements and length (L) is defined as the larger of the 2 measurements. The Examples may be shown to exhibit inhibition of tumor growth in the 116HCT tumor xenograph model.

Indications

The compounds of the invention have Aurora kinase modulatory activity in general, and inhibitory activity in particular. In one embodiment of the invention, there is provided a method of modulating Aurora kinase enzyme in a subject, the method comprising administering to the subject an effective dosage amount of a compound of a compound of Formulas I-II. As such, the compounds of the invention may be used to treat cellular proliferation disorders, including uncontrolled cell growth and aberrant cell cycle regulation. The compounds are also useful for treating disorders related to hyperproliferation of cells in normal tissue, including without limitation, non-tumor bearing metastatic tissue. For example, one use may be to protect normal hair follicles from chemotherapy induced alopecia.

In addition, compounds of the invention are useful for, but not limited to, the prevention or treatment of cancer and other Aurora kinase-mediated diseases or disorders. For example, compounds of the invention would be useful for the treatment of various solid and hematologically derived tumors, such as carcinomas, including, without limitation, cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compound of the invention may also be used to treat chemotherapy-induced thrombocytopenia, since the compounds may increase platelet count be increasing the rate of megakaryocyte maturation.

The compounds would also be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

In one embodiment of the invention, the compounds of Formulas I or II are useful to the treatment of a cancer selected from breast cancer, colon cancer, colorectal cancer, lung cancer, lymph cancer, hematopoeitic cancers, stomach cancer, ovarian cancer, pancreatic cancer, non-small cell lung cancer, thyroid cancer, prostate cancer, kidney cancer, liver cancer, bladder cancer, esophageal cancer, skin cancer or a combination thereof, in a subject, by administering to the subject an effective dosage amount of the compound of Formula I or II.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity. The compounds of the invention are also useful in the treatment of ocular conditions such as ocular and macular edema, ocular neovascular disease, scleritis, radial keratotomy, uveitis, vitritis, myopia, optic pits, chronic retinal detachment, postlaser complications, glaucoma, conjunctivitis, Stargardt's disease and Eales disease in addition to retinopathy and macular degeneration.

The compounds of the invention are also useful in the treatment of cardiovascular conditions such as atherosclerosis, restenosis, arteriosclerosis, vascular occlusion and carotid obstructive disease.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention can also be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations

Also embraced within this invention is a class of pharmaceutical compositions, also referred to as medicaments, comprising the active compounds of Formulas I-II in association with one or more non-toxic, pharmaceutically-acceptable excipients and/or carriers, diluents and/or adjuvants (collectively referred to herein as "excipient" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable excipients, including carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable excipient, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the excipients, carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy or with neoplastic or cytotoxic agents.

If formulated as a fixed dose, such combination products employ the compounds of this invention within the accepted dosage ranges. Compounds of Formulas I-III may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

There are large numbers of anti-neoplastic agents available in commercial use, in clinical evaluation and in pre-clinical development, which would be selected for treatment of neoplasia by combination drug chemotherapy. Such anti-neoplastic agents fall into several major categories, namely, antibiotic-type agents, alkylating agents, anti-metabolite agents, hormonal agents, immunological agents, interferon-type agents and a category of miscellaneous agents.

Alternatively, the compounds of the invention may also be used in co-therapies with other anti-neoplastic agents, such as other kinase inhibitors including angiogenic agents such as VEGFR inhibitors, p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing is merely illustrative of the invention and is not intended to limit the invention to the disclosed compounds. Variations and changes, which are obvious to one skilled in the art, are intended to be within the scope and nature of the invention, which are defined in the appended claims. All mentioned references, patents, applications and publications, are hereby incorporated by reference in their entirety, as if here written.

What is claimed is:
1. A compound of Formula I:

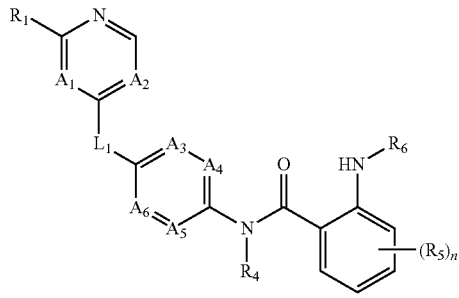

or a pharmaceutically acceptable salt thereof, wherein
each of $A^1$ and $A^2$, independently, is N or $CR^2$, provided no more than one of $A^1$ and $A^2$ is N;
each of $A^3$, $A^4$, $A^5$ and $A^6$, independently, is N or $CR^3$, provided that no more than two of $A^3$, $A^4$, $A^5$ and $A^6$ is N;
$L^1$ is —O— or —S—;
$R^1$ is acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)_2R^7$, —$S(O)_2R^7$, —$S(O)_2NR^7R^7$, —$NR^7S(O)_2NR^7R^7$, —$NR^7S(O)_2R^7$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl and ring of said ring system is optionally substituted independently with 1-5 substituents of $R^7$;

each $R^2$, independently, is H, halo, haloalkyl, haloalkoxyl, CN, OH, SH, $NO_2$, $NH_2$, methyl, ethyl, propyl, isopropyl, $C_{1-4}$-alkylamino-, $C_{1-4}$-dialkylamino-, $C_{1-4}$-alkoxyl, $C_{1-4}$-thioalkoxyl or acetyl;

alternatively, when $A^1$ is $CR^2$, then $R^2$ and $R^1$ taken together with the carbon atoms to which they are attached form a 6-membered ring of carbon atoms optionally including one or two nitrogen atoms, and optionally substituted with 1-3 substituents of $R^{1a}$, wherein each $R^{1a}$ is acetyl, $C_{1-10}$-alkyl, $C_{2-10}$-alkenyl, $C_{2-10}$-alkynyl, $C_{3-10}$-cycloalkyl, —$SR^7$, —$OR^7$, —$NR^7R^7$, —$C(O)R^7$, —$COOR^7$, —$OC(O)R^7$, —$C(O)C(O)R^7$, —$C(O)NR^7R^7$, —$NR^7C(O)R^7$, —$NR^7C(O)NR^7R^7$, —$NR^7(COOR^7)$, —$OC(O)NR^7R^7$, —$S(O)_2R^7$, —$S(O)_2R^7$, —$S(O)_2NR^7R^7$, —$NR^7S(O)_2NR^7R^7$, —$NR^7S(O)_2R^7$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl and ring of said ring system is optionally substituted independently with 1-5 substituents of $R^7$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^7$;

$R^4$ is H or methyl;

each $R^5$, independently, is halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^7$;

$R^6$ is acetyl, $C_{1-10}$-alkyl, $C_{2-10}$-alkenyl, $C_{2-10}$-alkynyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl and ring of said ring system is optionally substituted independently with 1-5 substituents of $R^7$;

each $R^7$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-6}$-alkyl, —$C(O)NHC_{1-6}$-alkyl, —$NHC(O)C_{1-6}$-alkyl, —$S(O)C_{1-6}$-alkyl, —$S(O)_2NHC_{1-6}$-alkyl, —$NHS(O)_2C_{1-10}$-alkyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

2. The compound of claim 1, or a pharmaceutically acceptable salt thereof, wherein $A^1$ is $CR^2$, wherein $R^2$ and $R^1$ taken together with the carbon atoms to which they are attached form a ring of

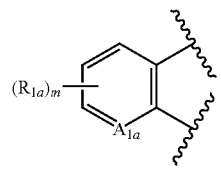

wherein $A^{1a}$ is N or CH;

$R^{1a}$ is acetyl, $C_{1-10}$-alkyl, $C_{2-10}$-alkenyl, $C_{2-10}$-alkenyl, $C_{3-10}$-cycloalkyl, $-SR^7$, $-OR^7$, $-NR^7R^7$, $-C(O)R^7$, $-COOR^7$, $-OC(O)R^7$, $-C(O)C(O)R^7$, $-C(O)NR^7R^7$, $-NR^7C(O)R^7$, $-NR^7C(O)NR^7R^7$, $-NR^7(COOR^7)$, $-OC(O)NR^7R^7$, $-S(O)_2R^7$, $-S(O)_2R^7$, $-S(O)_2NR^7R^7$, $-NR^7S(O)_2NR^7R^7$, $-NR^7S(O)_2R^7$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from 0, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^7$; and m is 0, 1 or 2.

3. The compound of claim 1, or a pharmaceutically acceptable salt thereof, wherein $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl.

4. The compound of claim 1, or a pharmaceutically acceptable salt thereof, wherein at least one of $A^3$, $A^4$, $A^5$ and $A^6$, independently, is N.

5. The compound of claim 1, or a pharmaceutically acceptable salt thereof, wherein each of $A^3$, $A^4$, $A^5$ and $A^6$, independently, is $CR^3$ and each $R^3$, independently, is H, F, Cl, Br, $CF_3$, $C_2F_5$, CN, OH, SH, $NO_2$, $NH_2$, methyl, ethyl, propyl, cyclopropyl, $CH_3NH-$, $CH_3O-$, $CH_3S-$ or $-C(O)CH_3$.

6. The compound of claim 1, or a pharmaceutically acceptable salt thereof, wherein each of $A^1$ and $A^2$, independently, is $CR^2$, and each $R^2$, independently, is H, F, Cl, Br, $CF_3$, CN, OH, SH, $NO_2$, $NH_2$, methyl, ethyl, $CH_3NH-$, $CH_3O-$, $CH_3S-$ or $-C(O)CH_3$; and $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl.

7. The compound of claim 1 having a Formula II:

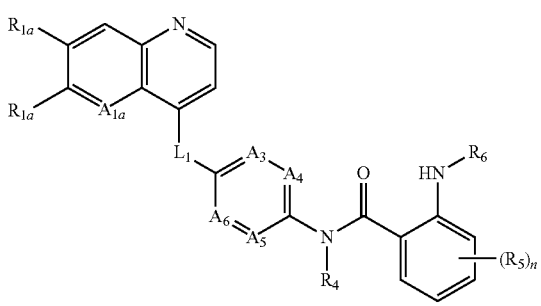

II or a pharmaceutically acceptable salt thereof, wherein $A^{1a}$ is N or $CR^2$, wherein $R^2$ is H, F, Cl, Br, $CF_3$, CN, OH, SH, $NO_2$, $NH_2$, methyl, ethyl, $CH_3NH-$, $CH_3O-$, $CH_3S-$ or $-C(O)CH_3$;

each of $A^3$, $A^4$, $A^5$ and $A^6$, independently, is N or $CR^3$, provided that no more than two of $A^3$, $A^4$, $A^5$ and $A^6$ is N;

$L^1$ is $-O-$ or $-S-$;

each $R^{1a}$, independently, is H, acetyl, $C_{1-10}$-alkyl, $C_{2-10}$-alkenyl, $C_{2-10}$-alkynyl, $C_{3-10}$-cycloalkyl, $-SR^7$, $-OR^7$, $-NR^7R^7$, $-C(O)R^7$, $-C(O)NR^7R^7$, $-NR^7C(O)R^7$, $-NR^7C(O)NR^7R^7$, $-NR^7(COOR^7)$, $-S(O)_2R^7$, $-S(O)_2R^7$, $-S(O)_2NR^7R^7$, $-NR^7S(O)_2NR^7R^7$, $-NR^7S(O)_2R^7$ or a fully saturated or partially or fully unsaturated 3-8 membered monocyclic or a 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl and ring of said ring system is optionally substituted independently with 1-5 substituents of $R^7$;

each R³, independently, is H, F, Cl, Br, CF₃, C₂F₅, CN, OH, SH, NO₂, NH₂, methyl, ethyl, propyl, cyclopropyl, CH₃NH—, CH₃O—, CH₃S— or —C(O)CH₃;

R⁴ is H or methyl;

each R⁵, independently, is halo, haloalkyl, haloalkoxyl, oxo, CN, OH, SH, NO₂, NH₂, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —C(O)R⁷;

R⁶ is acetyl, $C_{1-10}$alkyl, $C_{2-10}$-alkenyl, $C_{2-10}$-alkynyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N or S, wherein each of the $C_{1-10}$-alkyl, $C_{2-10}$-alkenyl, $C_{2-10}$-alkynyl and ring of said ring system is optionally substituted independently with 1-5 substituents of R⁷;

each R⁷, independently, is H, halo, haloalkyl, haloalkoxyl, oxo, CN, OH, SH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, C(O)$C_{1-6}$-alkyl, —C(O)NHC$_{1-6}$-alkyl, —NHC(O)C$_{1-6}$-alkyl, S(O)C$_{1-6}$-alkyl, S(O)₂NHC$_{1-6}$-alkyl, NHS(O)₂$C_{1-10}$-alkyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, NO₂, NH₂, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and n is 0, 1, 2, 3 or 4.

8. The compound of claim 7, or a pharmaceutically acceptable salt thereof, wherein each $R^{1a}$, independently, is H, halo, CF₃, C₂F₅, haloalkoxyl, CN, OH, SH, NO₂, NH₂, acetyl, methyl, methoxyl, ethyl, ethoxyl, propyl, propoxyl, isopropyl, cyclopropyl, butyl, isobutyl, tert-butyl, cyclobutyl, pentyl, cyclopentyl, hexyl, cyclohexyl, methylamine, dimethylamine, ethylamine, diethylamine, propylamine, isopropylamine, dipropylamine, diisopropylamine, —C(O)R⁷, —COOR⁷, —C(O)NHR⁷, —NHC(O)R⁷, —NHC(O)NHR⁷, —NH(COOR⁷), —S(O)₂R⁷, —S(O)₂R⁷, —S(O)₂NHR⁷, —NHS(O)₂NHR⁷, —NHS(O)₂R⁷ or a ring selected from phenyl, pyridyl, pyrimidinyl, pyridazinyl, pyazinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, cyclopropyl, cyclobutyl, azetidinyl, cyclopentyl, cyclohexyl, cycloheptyl or pyranyl, said ring optionally substituted independently with 1-5 substituents of R⁷.

9. The compound of claim 1, or a pharmaceutically acceptable salt thereof, selected from N-(4-(6,7-dimethoxyquinolin-4-yloxy)phenyl)-2-(4-fluorophenylamino)benzamide;

N-(4-(6,7-dimethoxyquinolin-4-yloxy)phenyl)-2-(phenylamino)benzamide;

5-fluoro-N-(4-(7-methoxy-1,5-naphthyridin-4-yloxy)phenyl)-2-(phenylamino)benzamide;

N-(4-(7-methoxy-1,5-naphthyridin-4-yloxy)phenyl)-2-(phenylamino)benzamide;

N-(4-(6,7-dimethoxyquinolin-4-yloxy)phenyl)-2-(3-fluorophenylamino)benzamide;

N-(3-fluoro-4-(7-methoxyquinolin-4-yloxy)phenyl)-2-(phenylamino)benzamide;

N-(4-(2-aminopyrimidin-4-yloxy)phenyl)-2-(4-fluorophenylamino)benzamide;

N-(4-(7-methoxy-1,5-naphthyridin-4-ylthio)phenyl)-2-(piperidin-1-ylamino)benzamide;

N-(4-(7-methoxy-1,5-naphthyridin-4-yloxy)phenyl)-2-(piperidin-1-ylamino)benzamide;

N-methyl-4-(4-(2-(phenylamino)benzamido)phenoxy)picolinamide; and

N-(4-(7-methoxy-1,5-naphthyridin-4-ylthio)phenyl)-2-(4-methoxypiperidin-1-ylamino)benzamide.

10. A pharmaceutical composition comprising a pharmaceutically acceptable excipient and an effective dosage amount of the compound of claim 1.

11. A method of treating a disorder mediated by the activity of Aurora kinase in a subject, the method comprising administering to the subject an effective dosage amount of the compound of claim 1.

12. The method of claim 11 wherein the disorder is one or more of (a) a solid tumor selected from cancer of the colon, and cervix.

13. A method of making a compound of claim 1, the method comprising the step of reacting compound of Formula A

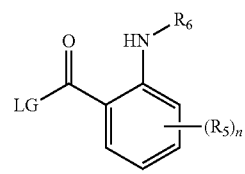

A with a compound of Formula B

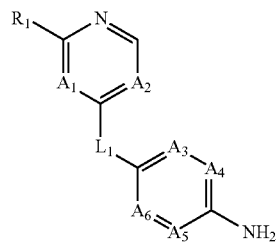

B wherein LG is a leaving group, R⁵, R⁶ and n of the compound of formula A and A¹, A², L¹, R¹ and $A^{3-6}$ of the compound of formula B are as defined in claim 1, to make a compound of Formula I.

* * * * *